United States Patent
Ahimou et al.

(10) Patent No.: US 10,947,577 B2
(45) Date of Patent: Mar. 16, 2021

(54) BIOLOGICAL STERILIZATION INDICATOR DEVICES AND METHODS OF USE

(71) Applicant: 3M INNOVATIVE PROPERTIES COMPANY, St. Paul, MN (US)

(72) Inventors: Francois Ahimou, Woodbury, MN (US); Sailaja Chandrapati, Woodbury, MN (US); Kurt J. Halverson, Lake Elmo, MN (US); Heather M. Webb, Woodbury, MN (US); Michael G. Williams, Vadnais Heights, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 945 days.

(21) Appl. No.: 14/377,203

(22) PCT Filed: Feb. 11, 2013

(86) PCT No.: PCT/US2013/025500
§ 371 (c)(1),
(2) Date: Aug. 7, 2014

(87) PCT Pub. No.: WO2013/122852
PCT Pub. Date: Aug. 22, 2013

(65) Prior Publication Data
US 2015/0337354 A1    Nov. 26, 2015

Related U.S. Application Data

(60) Provisional application No. 61/599,703, filed on Feb. 16, 2012.

(51) Int. Cl.
*C12Q 1/22* (2006.01)
*G01N 21/64* (2006.01)

(52) U.S. Cl.
CPC ........... *C12Q 1/22* (2013.01); *G01N 21/6428* (2013.01); *G01N 2201/061* (2013.01)

(58) Field of Classification Search
CPC . C12Q 1/22; G01N 21/6428; G01N 2201/061
USPC .......................................................... 435/31
See application file for complete search history.

(56) References Cited

U.S. PATENT DOCUMENTS

| | | | |
|---|---|---|---|
| 5,073,488 A | 12/1991 | Matner et al. | |
| 5,223,401 A | 6/1993 | Foltz et al. | |
| 5,252,484 A | 10/1993 | Matner et al. | |
| 5,418,167 A | 5/1995 | Matner et al. | |
| 5,567,598 A * | 10/1996 | Stitt ......................... | C12Q 1/04 435/29 |
| 5,770,393 A | 6/1998 | Dalmasso et al. | |
| 6,627,159 B1 | 9/2003 | Bedingham et al. | |
| 6,734,401 B2 | 5/2004 | Bedingham et al. | |
| 6,814,935 B2 | 11/2004 | Harms et al. | |
| 7,045,343 B2 | 5/2006 | Witcher et al. | |
| 2004/0121471 A1 | 6/2004 | Dufresne et al. | |
| 2004/0241783 A1* | 12/2004 | Papkovsky ......... | B01L 3/50853 435/33 |
| 2007/0252098 A1 | 11/2007 | Schmidt et al. | |
| 2011/0182770 A1 | 7/2011 | Chandrapati et al. | |

FOREIGN PATENT DOCUMENTS

| | | | |
|---|---|---|---|
| CA | 2 066 329 | 10/1992 | |
| EP | 0 934 428 | 8/1999 | |
| EP | 1 510 817 | 3/2005 | |
| JP | 2005-62178 | 3/2005 | |
| WO | WO 1998/15645 | 4/1998 | |
| WO | WO 1998/54354 | 12/1998 | |
| WO | WO 2000/11205 | 3/2000 | |
| WO | WO 2002/01180 | 1/2002 | |
| WO | WO 2002/01181 | 1/2002 | |
| WO | WO 2003/052019 | 6/2003 | |
| WO | WO 2005/054028 | 6/2005 | |
| WO | WO 2010/045138 | 4/2010 | |
| WO | WO 2010/045138 A2 * | 4/2010 | ............... C12Q 1/22 |
| WO | WO 2010/045517 | 4/2010 | |

OTHER PUBLICATIONS

Hutter, B. et al.; "Evaluation of OxoPlate for Teal-Time Assessment of Antibacterial Activities"; Current Microbiology; vol. 48; 2004; pp. 57-61.

O'Neal, D. et al.; "Oxygen Sensor Based on the Fluorescence Quenching of a Ruthenium Complex Immobilized in a Biocompatible Poly(Ethylene Glycol) Hydrogel"; IEEE Sensors Journal; vol. 4, No. 6, 2004; pp. 728-734.

Brochure entitled "3M™ Attest™ 1292E Rapid Readout Biological Indicator—Product Profile—3M Sterilization Assurance Program"; 3M Health Care Limited; 1999; 20 pgs.

O'Neal, P. "Oxygen Sensor Based on the Fluorescence Quenching of a Ruthenium Complex Immobilized in a Biocompatible Poly(Ethylene Glycol) Hydrogel," IEEE Sensors Journal, vol. 4, No. 6, Dec. 2004, p. 728-734.

* cited by examiner

*Primary Examiner* — Nghi V Nguyen
*Assistant Examiner* — Natalie M Moss
(74) *Attorney, Agent, or Firm* — 3M Innovative Properties Company; Trisha D. Adamson

(57) ABSTRACT

A biological sterilization indicator device is provided. The device comprises a body, a plurality of test microorganisms, and an oxygen-modulated first fluorescent sensor. The body comprises a first layer attached to a second layer, forming at least one isolatable microchamber and at least one primary passageway that provides fluidic communication between ambience and the at least one microchamber. The microchamber has an isolated volume of about 0.5 microliters to about 9.5 microliters. The plurality of test microorganisms and the oxygen-modulated first fluorescent sensor are disposed in the microchamber. A method of using the device to determine the effectiveness of a sterilization process is also provided.

18 Claims, 8 Drawing Sheets

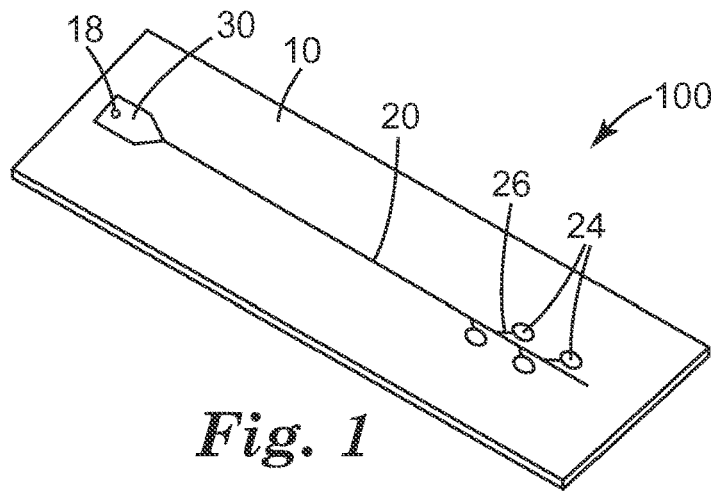
*Fig. 1*
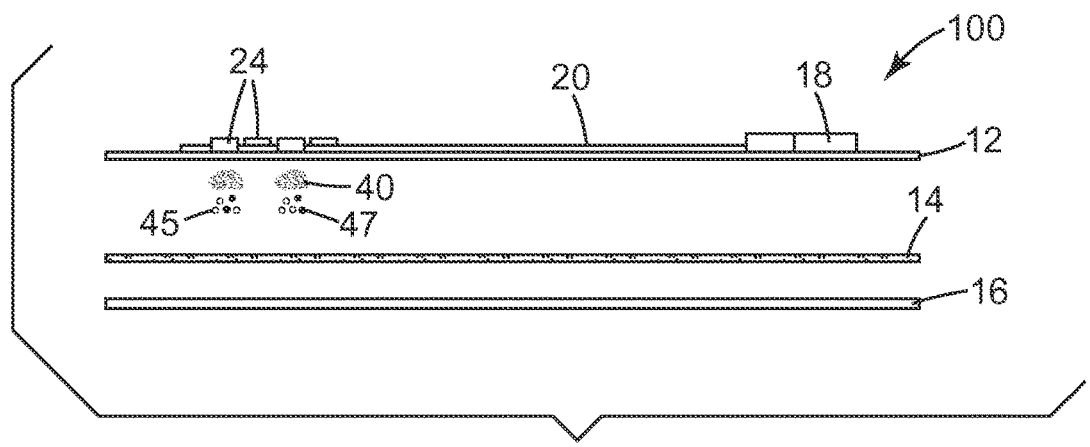
*Fig. 2*
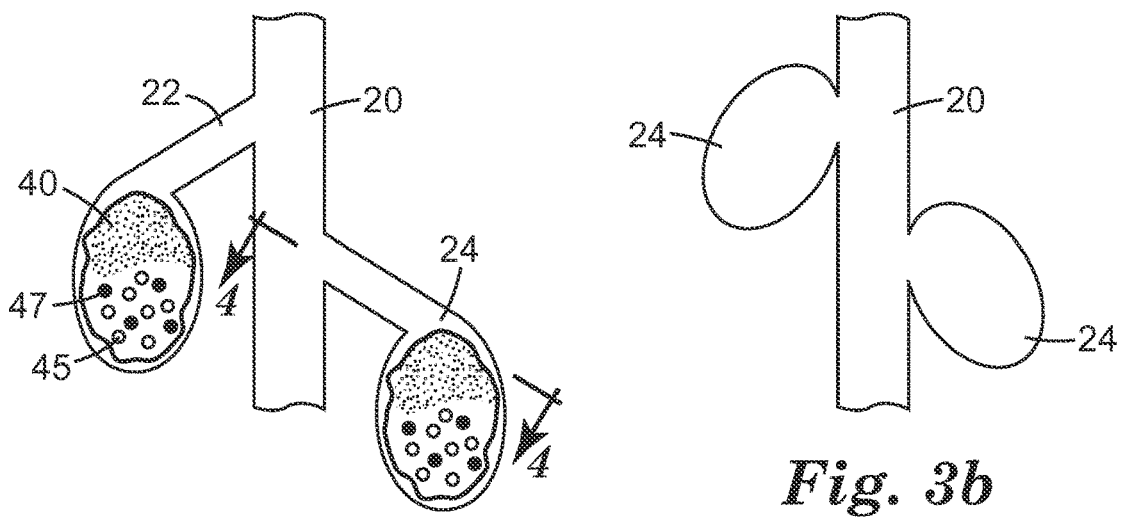
*Fig. 3a*  *Fig. 3b*

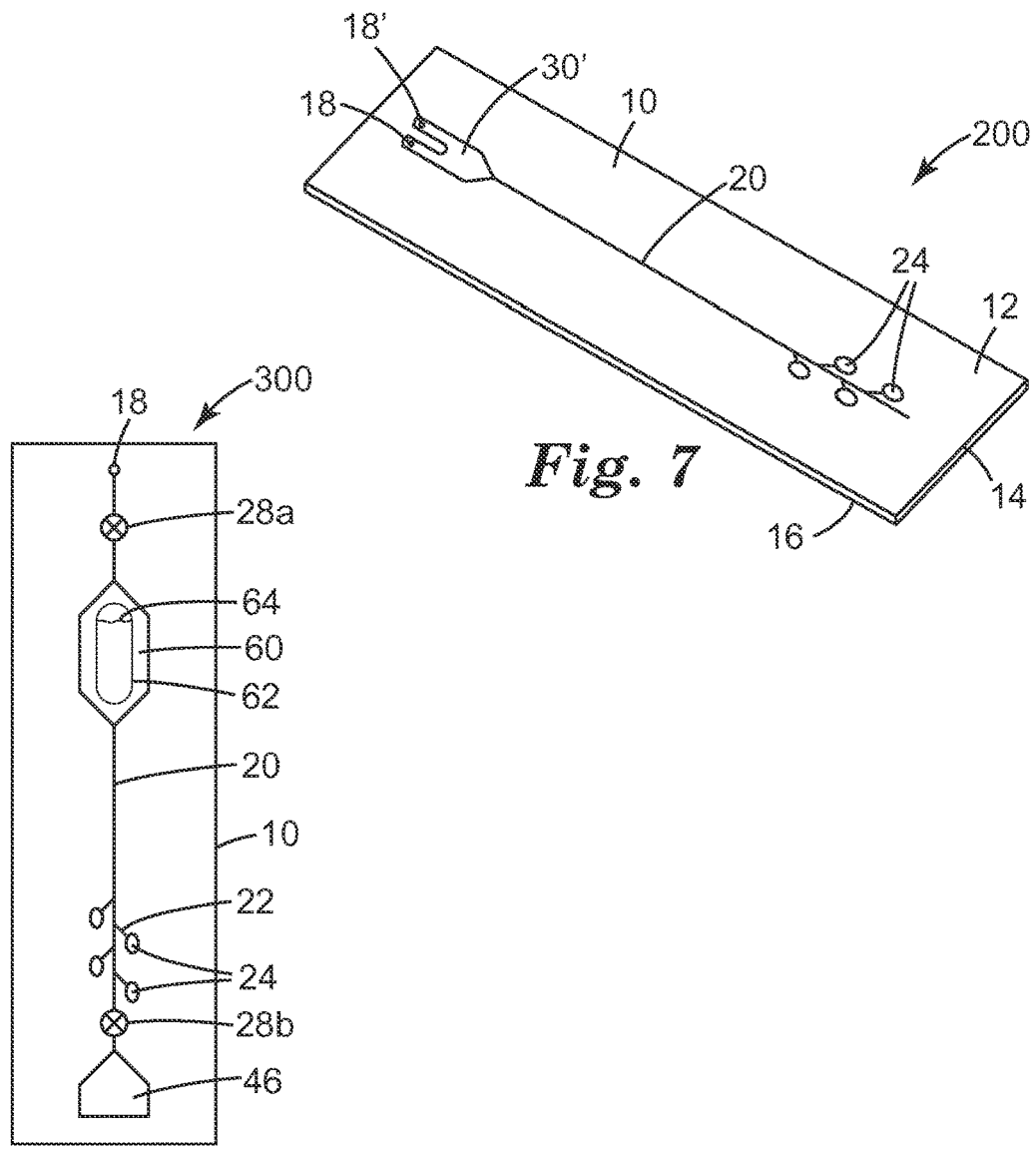
Fig. 7
Fig. 8
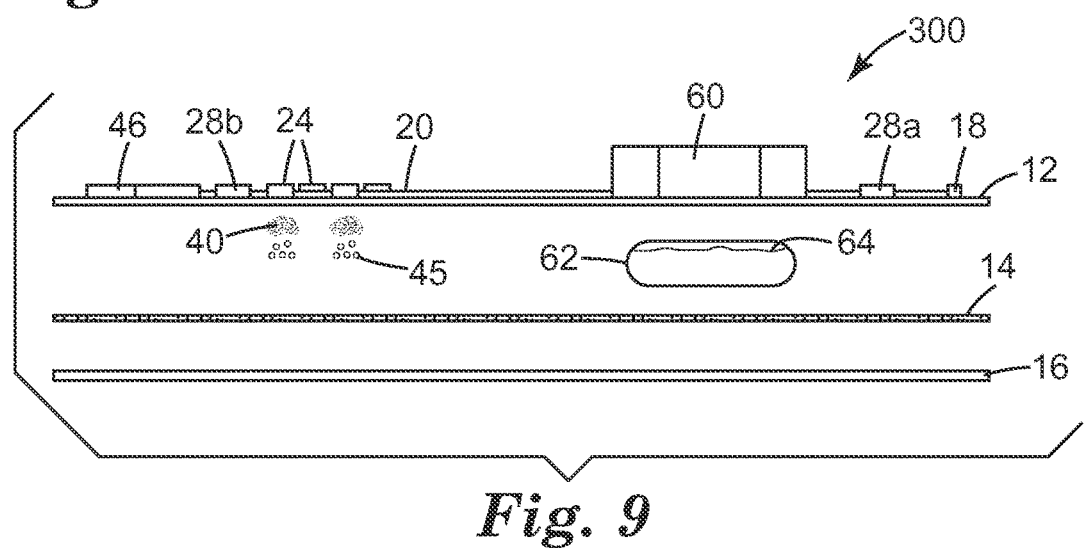
Fig. 9

BIOLOGICAL STERILIZATION INDICATOR DEVICES AND METHODS OF USE

CROSS REFERENCE TO RELATED APPLICATIONS

This application claims the benefit of U.S. Provisional Patent Application No. 61/599,703, filed Feb. 16, 2012, which is incorporated herein by reference in its entirety.

BACKGROUND

In a variety of industries, such as the health care industry but also in other industrial applications, it can be necessary to monitor the effectiveness of processes used to sterilize equipment such as medical devices, instruments and other non-disposable articles. In these settings, sterilization is generally defined as the process of completely destroying all viable microorganisms including structures such as viruses and spores. As a standard practice, hospitals include a sterility indicator with a batch of articles to assay the lethality of the sterilization process. Both biological and chemical sterility indicators have been used.

One standard type of biological sterility indicator includes a known quantity of test microorganisms, for example *Geobacillus stearothermophilus* (formerly *Bacillus stearothermophilus*) or *Bacillus atrophaeus* (formerly *Bacillus subtilis*) spores, which are many times more resistant to sterilization processes than most contaminating organisms. After the indicator is exposed to the sterilization process, the spores can be incubated in a nutrient medium to determine whether any of the spores survived the sterilization process, with spore growth indicating that the sterilization process was insufficient to destroy all of the microorganisms. Although advances have been made, the time period for determining this with certainty can be undesirably long.

Available chemical sterility indicators can be read immediately at the end of the sterilization process. However, the results indicate only that a particular condition was present during the sterilization process, such as the presence of a particular chemical or a temperature for a certain period of time.

In spite of these advancements, there remains a need for improved biological sterility indicators, which can indicate the effectiveness of a sterilization process without an excessive delay after completion of the sterilization process, and yet can provide a high level of confidence that various sterility parameters were reached in the sterilization process.

SUMMARY

In general, the present disclosure provides methods and devices for determining the effectiveness of a sterilization process. The biological sterilization indicator devices include microchambers that contain an oxygen-modulated fluorescent sensor useful in detecting a test microorganism that has survived a sterilization process. Advantageously, the use of the fluorescent sensor in a microchamber having a volume of 9.5 microliters or less permits rapid detection of one or more said surviving test microorganisms.

Biological sterilization indicator devices of the present disclosure optionally may comprise a plurality of microchambers, each microchamber comprising a plurality of test microorganisms and an oxygen-modulated fluorescent sensor. Advantageously, in one aspect, each of the plurality of microchambers may comprise the same test microorganism, thereby providing a device with replicate independent tests monitor the reproducibility of the effectiveness of a single sterilization process on the test microorganism. Alternatively, or additionally, the plurality of microchambers may include one or more microchambers containing a first test microorganism and one or more microchambers containing a second test microorganism. In this embodiment, the biological sterilization indicator device can be used to monitor one of a plurality of different sterilization processes (e.g., the biological sterilization indicator device may be used to monitor a steam sterilization process or an ethylene oxide sterilization process.

In one aspect, the present disclosure provides a biological sterilization indicator device. The device can comprise a body comprising a first layer attached to a second layer, the body forming at least one isolatable microchamber having an isolated volume of about 0.5 microliters to about 9.5 microliters and at least one primary passageway that provides fluidic communication between ambience and the at least one microchamber. The device further can comprise a plurality of test microorganisms disposed in the microchamber and an oxygen-modulated first fluorescent sensor disposed in the microchamber.

In any embodiment of the device, the plurality of test microorganisms can comprise a first plurality of first test microorganisms disposed in a first isolatable microchamber. In this embodiment, the device further can comprise a second plurality of second test microorganisms disposed in a second isolatable microchamber and the oxygen-modulated first fluorescent sensor can be disposed in each of the first and second microchambers. The first test microorganisms and the second test microorganisms can comprise test microorganisms of the same species. Alternatively, the first test microorganisms can comprise test microorganisms of a different species than the second test microorganisms.

In any of the above embodiments, at least one of the pluralities of test microorganisms can comprise a plurality of spores. In any of the above embodiments, the device further can comprise at least one liquid-containing reservoir, the reservoir having a closed state in which the liquid is not in fluid communication with one or more of the microchambers and an open state in which the liquid is in fluid communication with at least one of the one or more of the microchambers. In any of the above embodiments, the at least one primary passageway can be adapted to provide selective fluidic communication between ambience and the at least one microchamber. In any of the above embodiments, the device further may comprise a second fluorescent sensor that is not substantially modulated by oxygen, wherein the second fluorescent sensor is disposed in at least one microchamber. In any of the above embodiments, the first and/or second fluorescent sensor can comprise a bead, a film, or a coating.

In any of the above embodiments, at least one of the pluralities of test microorganisms in at least one microchamber can consist of spores of the species *Geobacillus stearothermophilus* or spores from the species *Bacillus atrophaeus*. In any of the above embodiments, the device can comprise a first microchamber and a second microchamber, wherein the first plurality of test microorganisms in the first microchamber consists of spores of the species *Geobacillus stearothermophilus* and spores from the species *Bacillus atrophaeus*. In any of the above embodiments, the device can comprise a first microchamber and a second microchamber, wherein the first plurality of test microorganisms disposed in the first microchamber consists of spores of the genus *Geobacillus stearothermophilus*, wherein the second plurality of test microorganisms disposed in the second microchamber consists of spores of the genus *Bacillus atrophaeus*.

In any of the above embodiments, the liquid in the reservoir can be contained in a frangible container. In any of the above embodiments, the liquid can comprise a nutrient. In any of the above embodiments, the at least one isolatable microchamber can comprise a first wall and a second wall, wherein the first wall or second wall is substantially non-transmissive to wavelengths of light in the u.v.-visible electromagnetic spectrum. In any of the above embodiments, first wall can be more transmissive to wavelengths of light in the u.v.-visible electromagnetic spectrum than the second wall. In any of the above embodiments, the device further can comprise a secondary growth indicator system comprising a pH indicator. In any of the above embodiments, the device can comprise a first microchamber and a second microchamber, wherein the first microchamber has disposed therein a first plurality of test microorganisms consisting of at least about 10 times as many spores as a number of test microorganisms disposed in the second microchamber.

In another aspect, the present disclosure provides a biological sterilization indicator system. The system can comprise a biological sterilization indicator device according to any one of the above embodiments, a source of electromagnetic energy capable of stimulating the emission of a fluorescent signal by the first fluorescent sensor, and a detection device adapted to detect the fluorescent signal. In any embodiment, the detection device is configured to be optically coupled with the biological sterilization indicator device. In any embodiment, the source and the detection device can be positioned in a console that is configured to receive the biological sterilization indicator device and wherein, when the biological sterilization indicator device is received by the console, the biological sterilization indicator device is optically coupled with the detection device.

In yet another aspect, the present disclosure provides a method for determining the effectiveness of a sterilization process. The method can comprise providing a device according to any of the above embodiments; moving a sterilant into fluidic communication with the at least one microchamber to form sterilant-treated test microorganisms; contacting the sterilant-treated test microorganisms with a nutrient medium in at least one microchamber; isolating the at least one microchamber such that a total volume of the nutrient medium and sterilant-treated test microorganisms isolated in the at least one microchamber is about 9.5 microliters or less; after isolating the microchamber, incubating the device for a period of time; and detecting a presence or absence of a first fluorescent signal emitted by the first fluorescent sensor.

In any embodiment of the method, the device can comprise a first microchamber and a second microchamber, wherein moving a sterilant into fluid communication comprises moving the sterilant into fluid communication with the first and second microchambers.

In any embodiment of the method, the device can comprise a first microchamber and a second microchamber, wherein moving a sterilant into fluidic communication with the first microchamber to form sterilant-treated test microorganisms further comprises preventing movement of the sterilant into fluidic communication with the second microchamber; wherein detecting a presence or absence of a first fluorescent signal emitted by the first fluorescent sensor further comprises detecting a presence or absence of a first fluorescent signal emitted by the first fluorescent sensor in both the first microchamber and the second microchamber. In any embodiment of the method, contacting the sterilant-treated test microorganisms with the nutrient liquid further can comprise providing an external force to move the liquid into at least one microchamber. In any embodiment of the method, providing the external force can comprise providing a centripetal force.

In any embodiment of the method, detecting a presence or absence of a first fluorescent signal can comprise detecting the first fluorescent signal at a first time and detecting the first fluorescent signal at a second time after the first time. In any embodiment of the method, the device can comprise the second fluorescent sensor, wherein the second fluorescent sensor is disposed in at least one microchamber, wherein the method further comprises detecting a second fluorescent signal from the second fluorescent sensor. In any embodiment of the method, detecting the second fluorescent signal can comprise detecting the second fluorescent signal at a first time and detecting the second fluorescent signal at a second time after the first time. In any embodiment of the method, detecting the first or second fluorescent signal further can comprise measuring the intensity of the first or second fluorescent signal.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Deformable seal" (and variations thereof) means a seal that is formed by permanently deforming a material (with or without the use of a tool) to occlude a conduit.

The terms "comprises" and variations thereof do not have a limiting meaning where these terms appear in the description and claims.

As used herein, "a," "an," "the," "at least one," and "one or more" are used interchangeably. Thus, for example, a microchamber can be interpreted to mean "one or more" microchambers.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF THE DRAWINGS

FIG. 1 is a top perspective schematic view of one embodiment of a biological sterilization indicator according to the present disclosure.

FIG. 2 is an exploded side view of the biological sterilization indicator of FIG. 1.

FIG. 3a is an enlarged top view, partially in section, of a portion of the device of FIG. 1.

FIG. 3b is an enlarged top view, of a portion of an alternative device with a plurality of microchambers directly connected to the primary passageway.

FIG. 4 is a cross-sectional view of the portion of the device of FIG. 1, taken along line 4-4 in FIG. 3a.

FIG. 7 is a top perspective view of a biological sterilization indicator having a liquid receiving chamber with a plurality of openings according to the present disclosure.

FIG. 8 is a plan view of an embodiment of a biological sterilization indicator comprising a liquid-containing reservoir according to the present disclosure.

FIG. 9 is an exploded side view of the biological sterilization indicator of FIG. 8.

DETAILED DESCRIPTION

Figure 4:
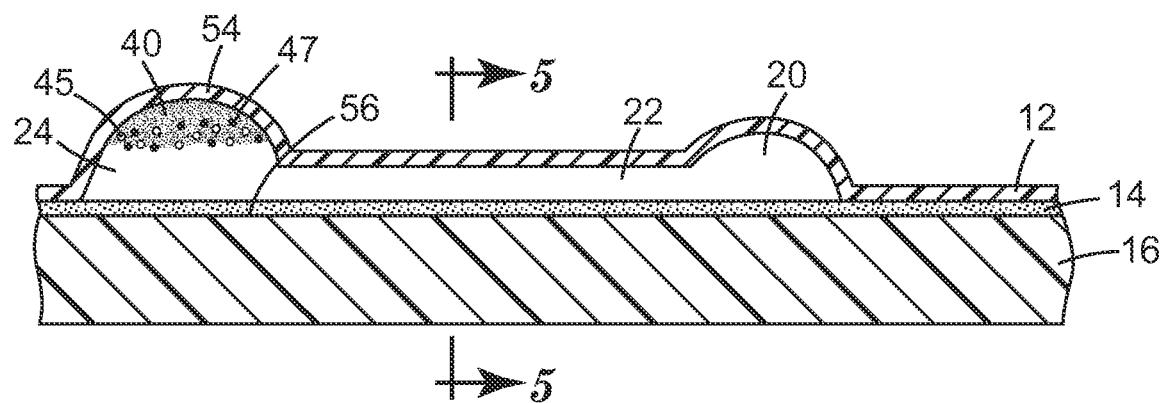

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the device, to indicate or imply necessary or required orientations of the device, or to specify how the invention described herein will be used, mounted, displayed, or positioned in use.

The present disclosure generally relates to a sterilization indicator and system, and particularly, to a biological sterilization indicator and system. A biological sterilization indicator is also sometimes referred to as a "biological sterility indicator," or simply, a "biological indicator." Some embodiments of the biological sterilization indicator of the present disclosure are self-contained, have a generally planar configuration, and include smaller volumes than prior indicators to facilitate rapid read-out and to improve the effectiveness of the biological sterilization indicator and system.

Generally, the microorganisms chosen to be used in a biological sterilization indicator are relatively resistant to the particular sterilization process for which they are chosen to monitor. The biological sterilization indicators of the present disclosure include a viable culture of a known species of microorganism, usually in the form of microbial spores. Bacterial spores, rather than the vegetative form of the organisms, are used at least partly because vegetative bacteria are known to be relatively easily killed by sterilizing processes. Spores also have superior storage characteristics and can remain in their dormant state for years. As a result, sterilization of an inoculum of a standardized spore strain provides a high degree of confidence that inactivation of all microorganisms in a sterilizing chamber has occurred.

By way of example only, the present disclosure describes the microorganisms used in the biological sterilization indicator as being "spores;" however, it should be understood that the type of microorganism (e.g., spore) used in a particular embodiment of the biological sterilization indicator is selected for being highly resistant to the particular sterilization process contemplated. Accordingly, different embodiments of the present disclosure may use different microorganisms, depending on the sterilization process for which the particular embodiment is intended.

The biological sterilization indicator system of the present disclosure can be used with a variety of sterilization processes including, but not limited to, exposure to steam, dry heat, gaseous or liquid agents (e.g., ethylene oxide, hydrogen peroxide, peracetic acid, ozone, or combinations thereof), radiation or combinations thereof. In at least some of the sterilization processes, an elevated temperature, for example, 50° C., 100° C., 121° C., 132° C., 134° C., or the like, is included or may be encountered in the process. In addition, elevated pressures may be encountered, for example, 15 psi ($1 \times 10^5$ Pa).

In general, the sterilization process includes placing the biological sterilization indicator of the present disclosure in a sterilizer. In some embodiments, the sterilizer includes a sterilization chamber that can be sized to accommodate a plurality of articles to be sterilized, and can be equipped with a means of evacuating air and/or other gases from the chamber and a means for adding a sterilant to the chamber. The biological sterilization indicator of the present disclosure can be positioned in areas of the sterilizer that are most difficult to sterilize (e.g., above the drain in a steam sterilizer). Alternately, the biological sterilization indicator of the present disclosure can be positioned adjacent (or in the general proximity of) an article to be sterilized when the biological sterilization indicator is positioned in the sterilization chamber. In addition, the biological sterilization indicator can be positioned in process challenge devices that can be used in sterilizers.

The sterilization process can further include exposing the article(s) to be sterilized and the biological sterilization indicator to a sterilant. The sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological sterilization indicator.

Turning to the drawings, FIG. 1 shows a perspective schematic view of one embodiment of a biological sterility indicator device 100 according to the present disclosure. FIG. 2 shows an exploded side view of the device 100 of FIG. 1. The device 100 comprises a body 10. The body 10 is formed by attaching (e.g., via an adhesive layer 14) a first layer 12 and a second layer 16 together. The body 10 comprises at least one microchamber 24. In the illustrated embodiment, the device 100 comprises a plurality of microchambers 24. The at least one microchamber 24 is in selective fluidic contact with ambient atmosphere via at least one opening 18. The selective communication can be modulated via a deformable seal, described below. The at least one opening 18 opens into a liquid-receiving chamber 30, which is in fluidic communication with the microchamber 24 via a primary passageway 20. The opening 18 is dimensioned to permit the access of a liquid transfer device (e.g., a pipet tip or a needle, not shown), thereby allowing the introduction of fluid into the fluid-receiving chamber while also permitting the egress of air out of the liquid-receiving chamber 30 as a volume of the air is displaced by a corresponding incoming volume of the liquid. The fluid pathway between the opening 18 and the microchamber 24 optionally may further comprise a feeder conduit 26.

The microchamber 24 defines a volume. In devices of the present disclosure, it may be preferred that the volume of the microchambers be about 9.5 microliters or less, alternatively about 5 microliters or less, and, in yet another alternative, about 2 microliter or less, and, in yet another alternative, about 1.5 microliter or less, and, in yet another alternative, about 1 microliter or less, and, in yet another alternative, about 0.5 microliters. The limited volume of liquid that can be contained in the microchamber 24 correspondingly limits the total amount of oxygen (e.g., dissolved oxygen) present in the microchamber when a liquid volume and/or a gas volume is isolated in the microchamber.

The body 10 comprises a first layer 12 and a second layer 16, between which the volume of microchamber 24 is disposed. In addition to the microchamber 24, the volumes of the primary passageway 20 and the liquid-receiving chamber 30 are also disposed between the first and second layers 12 and 16.

The microchamber 24 has a plurality of test microorganisms 40 (e.g., bacterial spores) disposed therein. In any embodiment, the plurality of test microorganisms is substantially pure (i.e., axenic). Bacterial spores used in a device of the present disclosure are selected according to the sterilization process in which the device will be used. For example, for a steam sterilization process, *Geobacillus stearothermophilus* or *Bacillus stearothermophilus* can be used. In another example, for an ethylene oxide sterilization process, *Bacillus atrophaeus* (formerly *Bacillus subtilis*) can be used. In any embodiment, the spores disposed in a microchamber 24 can include spores from at least one species including *Geobacillus stearothermophilus, Bacillus stearothermophilus, Bacillus subtilis, Bacillus atrophaeus, Bacillus megaterium, Bacillus coagulans,* and *Clostridium sporogenes, Bacillus pumilus*, or spores from a combination of any two or more of the foregoing species of test microorganisms. Thus, a device containing a combination of *Geobacillus stearothermophilus* spores and *Bacillus atrophaeus* spores, for example, could be used either in a steam sterilization process or in an ethylene oxide sterilization process.

As illustrated in FIGS. 1-11, biological sterilization indicator devices of the present disclosure may comprise a plurality of microchambers. It is contemplated that any microchamber of a particular device may contain a plurality of substantially pure (e.g., axenic) test microorganisms. It is further contemplated that any two or more microchambers of a particular device may contain a plurality of substantially pure test microorganisms of the same species or strain. Advantageously, this configuration of the device provides two independent tests using the same test microorganism in a unitary biological sterilization indicator device, thereby providing increased confidence in the validity of a sterilization test result.

It is even further contemplated that any microchamber of a particular device may contain a plurality of test microorganisms from two or more species or strains. Advantageously, in this configuration, a single device can be used to monitor one of at least two different types of sterilization processes. It is even further contemplated that at least one microchamber of a particular device may contain a plurality of substantially pure test microorganisms of one species and at least one other microchamber may contain a plurality of substantially pure test microorganisms of a different species. Advantageously, this configuration provides an alternative biological sterilization device that can also be used to monitor one of at least two different types of sterilization processes.

In some embodiments, a biological sterilization indicator device of the present disclosure may comprise a plurality of microchambers, wherein the device comprises a first microchamber and a second microchamber. The first microchamber has disposed therein a first plurality of test microorganisms consisting of at least about 10 times as many spores as a number of test microorganisms disposed in the second microchamber. Similarly, the device may further comprise a third microchamber having disposed therein about 10 times fewer test microorganisms than the second microchamber. Advantageously, the said device may be used to quantitatively assess the effectiveness of a sterilization process. That is, an effective sterilization process may kill all of the test microorganisms in the first through third microchambers. In contrast, a less effective sterilization process may only kill the test microorganisms in the third microchamber and an even less effective sterilization process may only kill the test microorganisms in the second and third microchambers.

The device 100 further comprises an oxygen-modulated first fluorescent sensor 45 disposed in the microchamber 24. Suitable oxygen-modulated fluorescent sensors include sensors comprising fluorescent compounds whose fluorescence is quenched by the presence of a sufficient concentration of molecular oxygen proximate the sensor. Nonlimiting examples of oxygen-modulated fluorescent compounds include transition metal (e.g., ruthenium-containing) complexes, including those described in an article entitled "Oxygen Sensor Based on the Fluorescence Quenching of a Ruthenium Complex Immobilized in a Biocompatible Poly (Ethylene Glycol) Hydrogel" by D. P. O'Neal et al. (IEEE Sensors Journal, 2004, Vol. 4, pp 728-734), which is incorporated herein by reference in its entirety. In any embodiment, the oxygen-modulated fluorescent compounds (e.g., dyes) may be suspended within or bound to a matrix (e.g., silicone rubber, silica gel, a polymer, or a sol-gel) to form the first fluorescent sensor 45. In any embodiment, the first fluorescent sensor 45 may be disposed in the microchamber 24 as a sheet-like object such as, for example, a coated layer. Alternatively, or additionally, the first fluorescent sensor 45 may be disposed in (e.g., incorporated into a polymer matrix) and/or on (e.g., incorporated into a coating) a particle or bead. In some embodiments, the oxygen-modulated first fluorescent sensor 45 may be disposed in the microchamber 24 as a plurality of beads.

Optionally, in any embodiment, the device 100 further comprises a second fluorescent sensor 47 disposed in the microchamber 24. Preferably, the fluorescence of the second fluorescent sensor 47 is not substantially modulated (i.e., the fluorescence is neither substantially enhanced nor substantially quenched) in the presence of molecular oxygen. Even more preferably, the fluorescence of the second fluorescent sensor 47 can be distinguished (e.g., by its absorbance and/or emission spectrum) from the fluorescence of the first fluorescent sensor 45. The second fluorescent sensor may comprise a fluorescent compound (e.g., dye) that is suspended within or bound to a matrix (e.g., silicone rubber, silica gel, a polymer, or a sol-gel) to form the second fluorescent sensor 47. In any embodiment, the second fluorescent sensor 47 may be disposed in the microchamber 24 as a sheet-like object such as, for example, a coated layer. Alternatively, or additionally, the second fluorescent sensor 47 may be disposed in (e.g., incorporated into a polymer matrix) and/or on (e.g., incorporated into a coating) a particle or bead. In some embodiments, the second fluorescent sensor 47 may be disposed in the microchamber 24 as a plurality of beads.

FIG. 3 shows an enlarged top view, partially in section, of a portion of the device of FIG. 1. In the illustrated embodiment, feeder conduits 22 fluidically connect the microchambers 24 with the primary passageway 20. The test microorganism 40, first fluorescent sensor 45 and second fluorescent sensor 47 are disposed in the interior of at least one microchamber 24. As described hereinbelow, deformation of the primary passageway 20 and/or a feeder conduit 22 can cause the isolation of a microchamber 24, thereby substantially preventing the subsequent contact of the contents of the isolated microchamber (not shown) with an oxygen-containing liquid or gas that may be present in the primary passageway 20 and/or the feeder conduit 22.

Biological sterilization indicator devices of the present disclosure include a sealing means that is used to substantially close the primary passageway 20, isolate the microchambers 24, or accomplish both closure of the primary passageway and isolation of the microchambers. Closing the passageway substantially prevents the ingress of oxygen-containing liquid or gas into an isolated microchamber 24. In any embodiment, the sealing means can comprise a deformable seal. As used in connection with the present disclosure, the deformable seals may be provided in a variety of locations and/or structures incorporated into the biological sterilization indicator devices. Essentially, however, the deformable seal in a biological sterilization indicator will be located somewhere in the fluid path between the opening and one or more microchambers.

With respect to FIG. 1, for example, the deformable seal may be located in the passageway 20 between the liquid-receiving chamber 30 and the plurality of microchambers 24. In this configuration the deformable seal may extend for the substantially the entire length of the primary passageway 20 or it may be limited to selected areas. For example, the deformable seal may extend along the primary passageway 20 only in the areas occupied by the feeder conduits 22 leading to the microchambers 24. In another example, the deformable seal may be a composite structure of discrete sealing points (not shown) located along the primary passageway 20 or within each of the feeder conduits 22.

Figure 5:
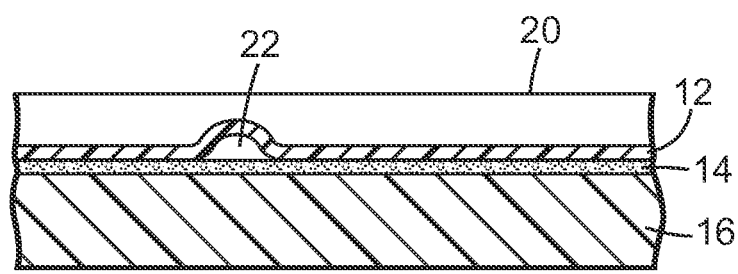
FIG. 5 is a cross-sectional view of the portion of FIG. 4, taken along line 5-5 in FIG. 4.
Figure 6:
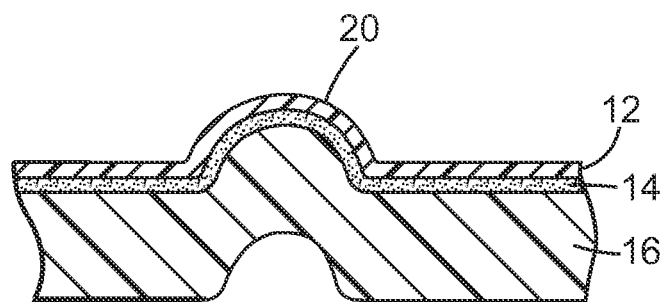
FIG. 6 is a cross-sectional view of the primary passageway of FIG. 4, taken after deformation of the primary passageway to isolate a microchamber.

Referring to FIGS. 4-6, one embodiment of a deformable seal for isolating the microchambers 24 is depicted. FIG. 4 shows the primary passageway 20 in an open (i.e., non-deformed) state. The primary passageway 20 is in fluidic communication with the microchamber 24 via the feeder conduit 22. The deformable seal is provided in the form of a deformable second layer 16 that can be deformed such that it extends into the primary passageway 20 as depicted in FIG. 6, thereby isolating the microchamber 24 and its contents from ambient air. The microchamber 24 has a test microorganism 40 and first and second fluorescent sensors (45 and 47, respectively) disposed therein. Referring back to FIG. 4, the microchambers 24 of the present disclosure comprise a first wall 54 and a second wall 56. The first wall 54 comprises a portion of the first layer 12 and the second wall 56 comprises a portion of the second layer 16. Also shown in FIG. 4 is the adhesive layer 14.

In any embodiment, the first and second walls (54 and 56, respectively) may be substantially transmissible to electromagnetic radiation having wavelengths in the ultraviolet and visible portions of the electromagnetic spectrum. In these embodiments, a fluorescent sensor (e.g., a first fluorescent sensor 45 and/or a second fluorescent sensor 47) present in the microchamber 24 may be irradiated with electromagnetic radiation (e.g., ultraviolet light) from a source facing the first wall 54 and/or the second wall 56 and any fluorescent light emitted from either of the first and/or second fluorescent sensor can be detected by a suitable detector (e.g., a CCD imaging device, a CMOS imaging device, or a diode array) facing the first wall and/or the second wall.

In any embodiment, at least one of the first or second walls (54 and 56, respectively) may comprise a material through which electromagnetic radiation having wavelengths in the ultraviolet and/or visible portions of the electromagnetic spectrum is substantially non-transmissible. This may be accomplished, for example, by fabricating the first layer 12 or second layer 16 with a pigment, dye or reflective material incorporated therein. Alternatively, a colored or reflective coating or layer may be positioned adjacent and, optionally, adhered to a portion of the first layer 12 or second layer 16 that forms the first wall 54 or second wall 56, respectively.

For example, the first wall 54 or second wall 56 can comprise a reflective portion (e.g., a white-colored portion or a metal, metal foil, or metal-coated surface). Advantageously, the reflective portion may serve to reflect fluorescent light emitted by the first fluorescent indicator so that the light is directed toward a detector (e.g., a human observer or an automated detector). In some embodiments, the first wall 54 or second wall 56 can comprise a black-colored portion. Advantageously, the black-colored portion may serve to provide a contrasting-colored surface against which the first fluorescent indicator can be observed and/or imaged.

Closure of the deformable seals may involve plastic deformation of portions of one or both layers 12 and 16 to occlude the primary passageways 20 and/or feeder conduits 22. The layer or layers may be deformed using a tool such as a stylus, for example. If, for example, a pressure sensitive adhesive 14 is used to attach the first and second layers 12 and 16 of the biological sterilization indicator device together, that same pressure sensitive adhesive may help to maintain occlusion of the primary passageways 20 and/or feeder conduits 22 by adhering the deformed first and second layers 12 and 16 together, as shown in FIG. 6. In addition, any conformability in the adhesive 14 may allow it to conform and/or deform to more completely fill and occlude the primary passageways 20 and/or feeder conduits 22.

The use of adhesive to attach the first layer 12 to the second layer 16 may enhance closure or occlusion of the deformable seal by adhering the two layers together within the primary passageway 20. It may be preferred that the adhesive 14 be a pressure sensitive adhesive in such an embodiment, although a hot melt adhesive may alternatively be used if deformation of the primary passageway 20 is accompanied by the application of thermal energy sufficient to activate the hot melt adhesive.

It should be understood, however, that complete sealing or occlusion of the deformed portions of the biological sterilization indicator device may not be required. For example, it may only be required that the deformation restrict flow, migration or diffusion (e.g., diffusion of an oxygen-containing liquid or gas) through a primary passageway, conduit or other fluid pathway sufficiently to provide the desired isolation. As used in connection with the present disclosure, "occlusion" will include both partial occlusion and complete occlusion (unless otherwise explicitly specified). Furthermore, occlusion of the primary passageway may be continuous over substantially all of the length of the primary passageway 20 or it may be accomplished over discrete portions or locations along the length of the primary passageway. Alternatively or additionally, closure of a deformable seal to isolate a microchamber may be accomplished by the occlusion of a feeder conduit alone and/or by occlusion of the feeder conduit/primary passageway junctions (in place of, or in addition to, occlusion of a portion or all of the length of the passageway).

In some embodiments in which the deformable seal is provided in the form of an occludable passageway, it may be advantageous to occlude the passageway over substantially all of its length and, in so doing, urge any sample materials within the passageway back towards a liquid-receiving chamber, if present, and/or toward a drain chamber, if present. It may be preferred that the sample materials urged back towards the liquid-receiving chamber are driven back into the liquid-receiving chamber. As a result, the liquid-receiving chambers in devices of the present disclosure may also serve as waste or purge chambers for materials urged out of the passageways and/or feeder conduits during closure of the deformable seals.

In any embodiment of the present disclosure, the biological sterility indicator device may include a liquid-receiving chamber adapted to facilitate the introduction of a liquid into the device. FIG. 7 shows a top perspective view of one embodiment of a biological sterility indicator device 200 with a liquid-receiving chamber 30' adapted to facilitate the reception of a liquid. In this embodiment, the liquid-receiving chamber 30' comprises two openings (18 and 18') with a liquid flow path through the liquid-receiving chamber 30' disposed there between. The liquid flow path is non-linear (in this case, the flow path is generally U-shaped), thereby facilitating the displacement of air from the liquid-receiving chamber 30' as a liquid is introduced through one of the openings (e.g., opening 18) and flows toward the other opening (e.g., opening 18').

In any embodiment, the biological sterility indicator device of the present disclosure optionally may comprise a liquid-containing reservoir. FIG. 8 shows a plan view of one embodiment of a device 300 comprising a liquid-containing reservoir 60 holding a liquid 64. In any embodiment, the liquid optionally may be contained in a frangible container 62 (e.g., a glass or plastic ampoule or a plastic pouch).

The liquid 64 can include a nutrient medium for the test microorganism. A nonlimiting example of a nutrient medium is a germination medium that will facilitate germination and/or outgrowth of surviving spores. In some embodiments, the liquid 64 can include water (or another solvent) that can be combined with nutrients to form a nutrient medium. Suitable nutrients can include nutrients necessary to promote germination and/or growth of surviving spores and may be provided in a dry form (e.g., powdered form, tablet form, caplet form, capsule form, a film or coating, entrapped in a bead or other carrier, another suitable shape or configuration, or a combination thereof) in the liquid-containing reservoir 60. Dry nutrients can be mixed in (e.g., dissolved in) the liquid 64 (e.g., sterile water) when the liquid is released from the frangible ampoule 62. By way of example only, in embodiments in which the nutrient medium is provided in a dry form, the dry form can be present within the liquid-containing reservoir 60, optionally, on a carrier (e.g., an absorbent material) or disposed in a substantially dehydrated hydrogel. In some embodiments, a combination of liquid and dry nutrient media can be employed. A person having ordinary skill in the art will recognize the nutrient or nutrients may be selected according to the metabolic capabilities of the test microorganism. One example of a nutrient medium to support the growth of spores is an aqueous medium containing 17 g/L bacteriological peptone and 0.17 g/L L-alanine with the pH adjusted to about 7.6. Optionally, the medium further may comprise a pH indicator (e.g., 0.03 g/l bromocresol purple).

The device 300 comprises a body 10 formed by attaching first layer 12 and a second layer 16, as described above. The body 10 comprises a plurality of microchambers 24. The device 300 comprises an opening 18 that is in fluidic communication with the plurality of microchambers 24 via a primary passageway 20, as described above. The device 300 further comprises an optional valve 28, which can selectively regulate fluid communication from the opening 18 to one or more microchambers 24. The valve 28 may take any form suitable for use in a microfluidic device including, for example, the valves described in U.S. Pat. Nos. 6,627, 159 and 6,734,401, which are incorporated herein by reference in their entirety. In the any embodiment, one or more microchamber 24 can be fluidically linked to the primary passageway 20 via an optional feeder conduit 22, as shown in FIG. 4. In some embodiments, the device 300 further comprises an optional drain chamber 46. The drain chamber 46 can function to receive excess fluid from a process intended to transfer a fluid (e.g., a nutrient medium) from the liquid-receiving chamber 30 or liquid-containing reservoir 60 to one or more of the plurality of microchambers 24.

Figure 10:
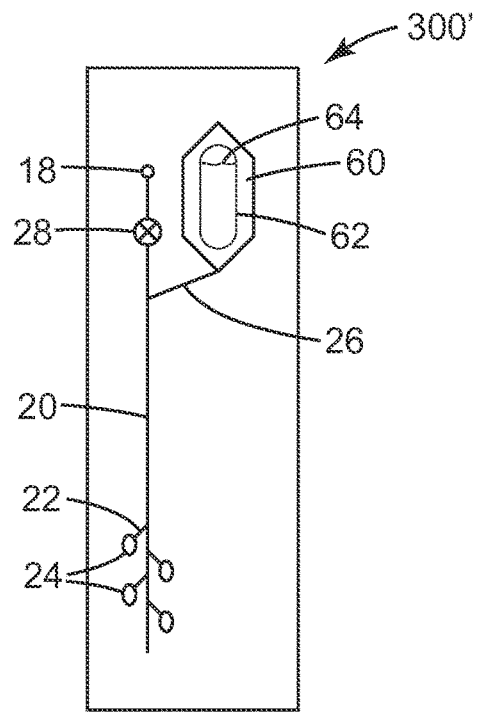
FIG. 10 is a plan view of an alternative embodiment of a biological sterilization indicator comprising a liquid-containing reservoir.

An alternative configuration for the device 300 of FIGS. 8 and 9, which device includes a liquid-containing reservoir 60 disposed along the fluidic pathway formed by the primary passageway 20, is shown in FIG. 10. FIG. 10 shows a plan view of a device 300' that includes a liquid-containing reservoir 60 that is fluidically connected to the primary passageway 20 via a branch conduit 26. Also shown in FIG. 10 are the opening 18, a plurality of microchambers 24, an optional valve 28, and a frangible container 62 containing a liquid 64 (e.g., a nutrient-containing liquid).

Figure 11:
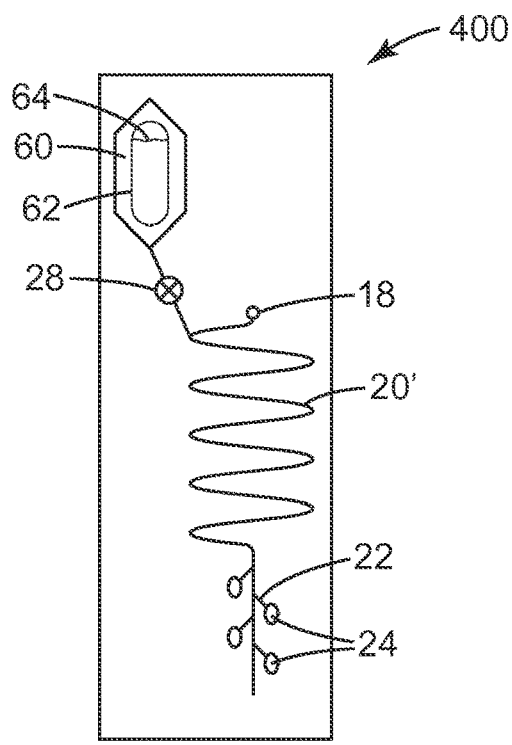
FIG. 11 is a plan view of one embodiment of a biological sterilization indicator having a tortuous fluidic pathway according to the present disclosure.

In any embodiment, a device of the present disclosure may comprise a primary passageway that defines a tortuous path that a sterilant gas must traverse in order to get from the opening to one or more microchambers. FIG. 11 shows a plan view of one embodiment of a biological sterilization indicator device 400 comprising a primary passageway 20' that defines a tortuous path from the opening 18 to a microchamber 24. Advantageously, the tortuous path can provide a more stringent challenge for a particular sterilization process and may be a better indicator of the penetration of a sterilant gas into the interior of a wrapped article or a lumened medical device, for example. Also shown in FIG. 11 are an optional liquid-containing reservoir 60 containing a frangible container 62 containing a liquid 64 (e.g., a nutrient-containing liquid). The liquid-containing reservoir 60 is fluidically connected to the primary passageway 20 via a branch conduit 26. The liquid-containing reservoir 60 optionally may be in selective fluid communication with the primary passageway 20 via a valve 28.

The first layer 12 and second layer 16 of any device of the present disclosure may be manufactured using a variety of suitable materials, which may be selected based upon the type of sterilization process in which the biological sterilization indicator will be used. Examples of suitable materials include polymeric materials (e.g., polypropylene, polyester, polycarbonate, polyethylene, etc.), metals (e.g., metal foils), etc. For biological sterilization indicators that may be used in ethylene oxide or hydrogen peroxide sterilization processes, it is particularly useful to fabricate the biological sterilization indicator using materials that permit rapid outgassing of any residual sterilant gas. In one embodiment, it may be preferred to form (e.g., using a molding or thermoforming process) in one layer (e.g., layer 12) of the device impressions, cavities, or depressions, for example, that create the shape that defines the volume of all of the nonplanar (i.e., 3-dimensional) features of the body 10; such as the liquid-receiving chamber, passageways, reservoirs, branch conduits, drain chamber, and microchambers. In this embodiment, the opposite layer (i.e., layer 16) is provided in a generally flat sheet-like configuration. For example, it may be preferred to provide all of the nonplanar features of a biological sterilization indicator in a polymeric sheet that has been molded, vacuum-formed, or otherwise processed to form the first layer 12 of a biological indicator device. In this example, the first layer 12 The second layer 16 can then be provided as, e.g., a substantially planar sheet of metal foil, polymeric material, multi-layer composite, etc. that is attached to the first layer 12 to complete formation of the 3-dimensional features of the body 10. It may be preferred that the materials selected for the layers of the device exhibit good barrier properties (e.g., resistant to the passage of water or gasses such as sterilant gasses and oxygen, for example, therethrough).

In an alternative embodiment, some of the nonplanar features of the body 10 can be created (e.g., by an embossing or thermoform process) in or on one layer (e.g., first layer 12) and some of the nonplanar features can be created in or on the other layer (e.g., second layer 16) and the two layers can be attached as described herein to form complete body 10 of the device 100.

It is also contemplated that at least one of the first layer 12 and second layer 16 include a metallic layer, e.g., a metallic foil. If provided as a metallic foil, the first layer or second layer may include a passivation layer on the surface of the first or second layers that face the interiors of the liquid-receiving chambers 30; primary passageways 20; liquid-containing reservoir 60, if present; feeder conduits 22, if present; and/or microchambers 24 to prevent contamination of the sample materials by the metal.

As an alternative to a separate passivation layer, any adhesive layer 14 used to attach the first layer 12 to the second layer 16 may also serve as a passivation layer to prevent contact between any materials (e.g., bacterial spores) and any metallic layer in the first layer 12 or second layer 16. The adhesive may also be beneficial in that it may be conformable. If so, the adhesive layer 14 may provide enhanced occlusion by filling and/or sealing irregularities or surface roughness present on either of the first or second layers (12 and 16, respectively).

The first and second layers 12 and 16 may be bonded to each other by any suitable technique or techniques, e.g., melt bonding, adhesives, combinations of melt bonding and adhesives, etc. If melt bonded, it may be preferred that both layers 12 and 16 include, e.g., polypropylene or some other melt bondable material, to facilitate melt bonding. It may, however, be preferred that the first and second layers 12 and 16 be attached using adhesive. As depicted in FIGS. 2 and 5, the adhesive may preferably be provided in the form of a layer 14 of adhesive. It may be preferred that the adhesive layer 14 be provided as a continuous, unbroken layer over the surface of at least one of the first and second layers 12 and 16. It may, for example, be preferred that the adhesive layer 14 be provided on the second layer 16 and, more particularly, it may be preferred that the adhesive layer 14 cover substantially the entire surface of the second layer 16 facing the first layer 12.

A variety of adhesives may be used, although any adhesive selected should be capable of withstanding the environmental conditions (e.g., heat, pressure, water vapor, sterilant gasses) used while processing a biological sterilization indicators and conditions (e.g., incubation temperature, exposure to ultraviolet light) used to detect the presence or absence of viable spores in a microchamber after the device has been subjected to a sterilization process. It may also be preferred that any adhesives used in connection with the biological sterilization indicator devices exhibit low fluorescence and be compatible the nutrient medium and substantially nontoxic to the microorganisms used in a biological sterility indicator.

It may be preferred to use adhesives that exhibit pressure sensitive properties. Such adhesives may be more amenable to high volume production of biological sterilization indicator devices since they typically do not involve the high temperature bonding processes used in melt bonding, nor do they present the handling problems inherent in use of liquid adhesives, solvent bonding, ultrasonic bonding, and the like. Suitable adhesives are described in International Patent Publication Number WO 02/01180, which is incorporated herein by reference in its entirety.

Biological sterilization indicator devices of the present disclosure comprise at least one fluorescent indicator composition (i.e., the first fluorescent sensor). Accordingly, in order to interpret a test result, the fluorescent sensor is illuminated with a source of electromagnetic radiation that is capable of interacting with the fluorescent indicator composition to cause fluorescence. The wavelengths of electromagnetic radiation capable of interacting with (e.g., being absorbed by) the fluorescent indicator composition to cause fluorescence are dependent upon the fluorophore used in the fluorescent sensor. An example of a suitable source of electromagnetic radiation for some fluorophores is a source of ultraviolet light (e.g., a hand-held ultraviolet light source or a plate reader comprising an ultraviolet light source).

Thus, in some embodiments, it may be preferable to dimension the biological sterilization indicator device of the present disclosure such that the device is configured to be used with a plate reader. Configured to be used with a plate reader can include dimensioning the device such that it operationally fits in a plate reader such that the one or more microchambers of the device are aligned with the optical system of the plate reader to permit illumination of the microchambers with suitable electromagnetic radiation and to permit detection of fluorescence in the microchambers. Configured to be used with a plate reader may alternatively mean the biological sterilization indicator device is dimensioned to fit in a carrier operationally fits in a plate reader and aligns the microchambers of the biological sterilization indicator device in order to detect fluorescence in the microchambers of the device when the carrier is placed into the plate reader.

When making biological indicator test devices of the present disclosure, the test microorganisms can be introduced into the microchamber using one or more of several methods. For example, the test microorganisms can be suspended in a suitable suspending medium (e.g., a liquid such as water or a buffer solution) to an appropriate concentration (e.g., $10^9$ spores/milliliter). In one embodiment, a suitable volume of the suspension (e.g., 1 microliter of water containing about $10^6$ spores) can be transferred (e.g. by pipet) to a depression (e.g., a depression in a first layer of a body) that defines the shape and location of a microchamber (e.g., microchamber 24 formed in first layer 12 shown in FIG. 5). The liquid suspending medium can be allowed to dry and the second layer subsequently can be attached to the first layer, thereby forming a microchamber with the plurality of spores disposed therein (not shown). The first and/or second fluorescent sensors likewise can be suspended in a liquid medium and transferred to the location defining a microchamber wherein the suspending medium is allowed to evaporate. Optionally, the suspension of test microorganisms further can comprise the first fluorescent sensor and/or second fluorescent sensor. In this embodiment, the test microorganism, the first fluorescent sensor, and the second fluorescent sensor, if present, all can be deposited simultaneously at a location that defines a microchamber in the biological sterilization indicator.

In an alternative embodiment, the first and second layers can be attached to form the body of the biological sterilization indicator device. Subsequently, a suitable volume of a suspension of test microorganisms (e.g., 1 microliter of water containing at least $10^5$ spores; preferably, about $10^6$ spores) can be transferred (e.g. by pipet) through the opening and can be urged into the microchamber using centrifugal force, as described herein. The suspending medium subsequently can be evaporated (e.g., by lyophilization), thereby leaving the spores (e.g., about $10^6$ spores) disposed in the microchamber. The first and/or second fluorescent sensors likewise can be suspended in a liquid medium, deposited into the opening and urged into the microchamber wherein the suspending medium is allowed to evaporate. Optionally, the suspension of test microorganisms further can comprise the first fluorescent sensor and/or second fluorescent sensor. In this embodiment, the test microorganism, the first fluorescent sensor, and the second fluorescent sensor, if present, all can be deposited simultaneously through the opening and urged into a microchamber in the biological sterilization indicator.

In some embodiments, the test microorganisms (e.g., spores) and/or the oxygen-modulated fluorescent sensor can be disposed in a coating adhered to a wall of the microchamber. Suitable coatings include, for example, a hydrophilic agent. The hydrophilic agent may comprise a polymer (e.g., a hydrophilic polymer that forms a hydrogel, such as a cellulosic polymer, agar, agarose, polyvinyl alcohol, polyvinylpyrollidone, polyethylene glycol, polyacrylamide, a derivative of any of the foregoing materials, or a combination of any two or more of the foregoing materials). Alternatively or additionally, the hydrophilic agent may include a nutrient to support the germination and/or outgrowth of a spore. In these embodiments, the hydrophilic coating material may be added to the suspension of test microorganisms when the suspension is incorporated into the device and the hydrophilic coating can be dried down with the suspension of test microorganisms.

In one method in which the microchambers 24 are isolated after distributing a nutrient liquid into the microchambers 24, it may be necessary to close the deformable seal along only a portion of the primary passageway 20 or, alternatively, the entire length of the primary passageway. Where only a portion of the primary passageway 20 is deformed, it may be preferred to deform that portion of the primary passageway 20 located between the liquid-receiving chamber 30, if present, and the microchambers 24.

Biological sterilization indicator devices may be processed alone, (e.g., without any accessory structure, as depicted in FIG. 1). In any embodiment, however, the biological sterilization indicator device may be mounted on a carrier. Suitable carriers are described in U.S. Pat. No. 6,627,159, which is incorporated herein by reference in its entirety. Advantageously, the carrier can facilitate handling the biological sterilization indicator devices and can facilitate the alignment of the microchannels with an automated reader, as described hereinbelow.

By providing a carrier that is separate from the biological sterilization indicator device, the biological sterilization indicator device can be subjected to a sterilization process and subsequently placed into a carrier that is adapted to be handled by automated equipment (e.g., robotic arms, etc.) processing in conventional equipment. Another potential advantage of a carrier is that the biological sterilization indicator devices may exhibit a tendency to curl or otherwise deviate from a planar configuration. Attaching the biological sterilization indicator device to a carrier can retain the biological sterilization indicator device in a planar configuration for processing.

Carriers used in connection with the biological sterilization indicator devices of the present disclosure preferably also have some preferred physical properties. For example, it may be preferred that the carriers provide limited areas of contact with the biological sterilization indicator devices to which they are mounted to reduce thermal transmission between the biological sterilization indicator device and the carrier. It may further be preferred that the carriers themselves have a relatively low thermal mass to avoid influencing temperature changes in the biological sterilization indicator devices.

If the biological sterilization indicator device is to be loaded using centrifugal forces developed during rotation of the biological sterilization indicator devices, the centrifugal forces may challenge the sealing of the microchambers and fluid pathways in the device. The challenges may be especially acute when the biological sterilization indicator device is constructed using an adhesive to attach two layers together. A properly designed carrier may assist in maintaining the integrity of the biological sterilization indicator device by providing the opportunity to apply pressure to the card during loading and/or during processing the biological sterilization indicator device in a sterilizer and/or in a centrifuge.

Although various constructions of illustrative embodiments are described herein, the body of a biological sterilization indicator of the present disclosure may be manufactured according to the principles described in U.S. Pat. Nos. 6,627,159 and 6,734,401; each of which is incorporated herein by reference in its entirety.

The documents identified above all disclose a variety of different constructions of devices that could be used to manufacture biological sterilization indicators according to the principles of the present disclosure. For example, although portions of the body of many of the biological sterilization indicators described herein are attached using adhesives (e.g., pressure sensitive adhesives), the body of biological sterilization indicators of the present disclosure could be manufactured using heat sealing or other bonding techniques.

Devices of the present disclosure can be sealed using a sealing apparatus. Nonlimiting examples of a suitable sealing apparatuses, and uses thereof, are shown and described in U.S. Pat. No. 6,627,159.

Devices of the present disclosure can be used in a method for determining the effectiveness of a sterilization process. Biological indicators and chemical indicators used to determine the efficacy of sterilization are well known in the art. In conventional biological indicators, a test organism which is many times more resistant to the sterilization process employed than most organisms which would be present by natural contamination, is coated on a carrier and placed in a sterilizer along with the articles to be sterilized. After completion of the sterilization cycle, the carrier is incubated in nutrient medium to determine whether any of the test organisms survived the sterilization procedure. Growth of a detectable number of organisms normally takes a minimum of twenty-four hours and can be detected by a pH change in the nutrient medium and/or by the hydrolysis of a fluorogenic enzyme substrate, as described in U.S. Pat. No. 5,073,488, which is incorporated herein by reference in its entirety.

As with other biological sterilization indicator devices known in the art, the devices of the present disclosure can be placed in a sterilization process along with articles to be sterilized. After the sterilization process, the test microorganism is contacted with a nutrient medium and incubated for a period of time to permit the germination and/or outgrowth of any test microorganism that may have survived the sterilization process. Without being bound by theory, the surviving sterilant-treated test microorganisms, if present, are detected by their ability to utilize the molecular oxygen present in the device via normal aerobic metabolism, thereby permitting increased fluorescence by an oxygen-modulated fluorescent sensor. Thus, the absence of any surviving test microorganism results in no substantial increase fluorescence of the oxygen-modulated fluorescent sensor when the sterilant-treated test microorganisms are contacted with the nutrient medium.

Figure 12:
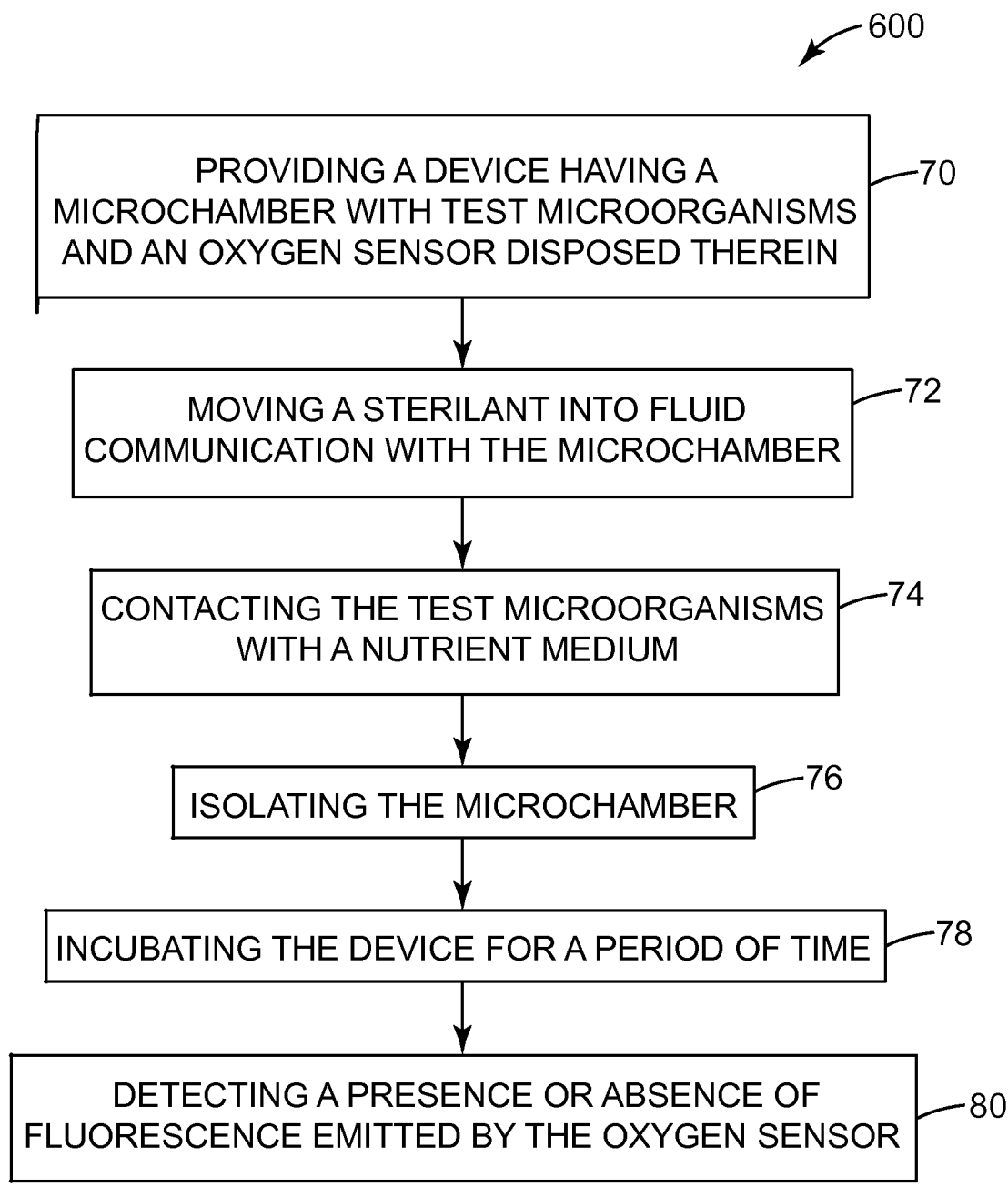
FIG. 12 is a block diagram of one embodiment of a method for determining the effectiveness of a sterilization process according to the present disclosure.

FIG. 12 shows a block diagram of one embodiment of a method 600 for determining the effectiveness of a sterilization process according to the present disclosure. The method comprises the step 70 of providing any biological sterilization indicator device according to the present disclosure, the device comprising a body comprising a first layer attached to a second layer, the body forming at least one isolatable microchamber having an isolated volume of about 0.5 microliters to about 9.5 microliters and at least one primary passageway that provides fluidic communication between ambience and the at least one microchamber; a plurality of test microorganisms disposed in the at least one microchamber; and an oxygen-modulated first fluorescent sensor disposed in the microchamber.

The method 600 further comprises the step 72 of moving a sterilant into fluidic communication with the at least one microchamber to form sterilant-treated test microorganisms. Moving a sterilant into fluidic communication with the at least one microchamber can comprise exposing the device to a sterilization process by, for example, exposing the device and the components thereof (e.g., test microorganisms) to moist steam in a steam sterilizer, exposing the device and the components thereof to ethylene oxide in an ethylene oxide sterilizer, exposing the device and the components thereof to hydrogen peroxide plasma in a hydrogen peroxide sterilizer, or exposing the device and the components thereof to ozone in an ozone sterilizer. When the biological sterilization indicator device comprises two or more microchambers, moving a sterilant into fluidic communication with a microchamber can comprise moving a sterilant simultaneously into fluidic communication with a plurality of microchambers.

The method 600 further comprises the step 74 of contacting the sterilant-treated test microorganisms with a nutrient medium in at least one microchamber. Contacting the sterilant-treated test microorganisms with a nutrient medium may comprise introducing a liquid; preferably a sterile liquid such as water, a buffer solution, or a nutrient medium as described herein; into an opening (e.g., opening 18 of FIG. 1) of the device and urging the liquid (e.g., by capillary action or by an external force such as a centripetal force provided by, for example, a centrifuge) into the at least one microchamber. Alternatively, or additionally, contacting the sterilant-treated test microorganisms with a nutrient medium may be accomplished by moving (e.g., by capillary action or by centripetal force using a centrifuge) a liquid; preferably a sterile liquid such as water, a buffer solution, or a nutrient medium as described herein; from a liquid-containing reservoir, if present in the device, into the at least one microchamber. Moving a liquid from the liquid-containing reservoir may further comprise breaching a frangible container to release the liquid and/or actuating a valve to open a fluidic pathway from the liquid-containing reservoir to the microchamber. Thus, contacting the sterilant-treated test microorganisms further may comprise changing a liquid-containing reservoir from a closed state to an open state. In some embodiments, moving a liquid from the liquid-containing reservoir may further comprise dissolving a substantially dehydrated nutrient (optionally, disposed in the device) to form the nutrient medium.

The method 600 further comprises the step 76 of isolating the at least one microchamber such that the total volume of the nutrient medium and sterilant-treated test microorganisms isolated in the at least one microchamber is about 9.5 microliters or less. The at least one microchamber can be isolated by actuating a deformable seal or a valve positioned in a primary passageway and/or a feeder conduit, as disclosed herein. Actuating the deformable seal and/or valve isolates a small volume (e.g., about 0.5 microliters to about 9.5 microliters) of the nutrient medium in the microchamber. Isolating the microchamber thereby prevents diffusive transfer of oxygen (e.g., through a liquid or a gas) along the primary passageway and/or feeder conduit to the microchamber. Advantageously, this limits the oxygen available in the microchamber to interact with the oxygen-modulated first fluorescent sensor. Accordingly, any surviving test microorganisms, if present, can metabolize the limited amount of oxygen in a relatively short period of time and, thereby, reduce the amount of quenching of the first fluorescent sensor. Thus, if the sterilization process has failed (i.e., there is at least one surviving sterilant-treated test microorganism, the surviving microorganism can be detected more rapidly than if it was present in a larger volume of nutrient medium.

In some embodiments, the total volume of the nutrient medium isolated in the microchamber may include a portion isolated in a feeder conduit that is fluidically connected to the microchamber. For example, if the microchamber is isolated by actuating a deformable seal in the primary passageway, there may be a portion of nutrient medium isolated in a feeder conduit that is fluidically connecting the isolated microchamber to the primary passageway. This condition is contemplated within the scope of the invention provided the total volume of liquid medium isolated in the feeder conduit and the microchamber does not exceed 9.5 microliters.

The method 600 further comprises the step 78 of incubating the device for a period of time. Typically, the device is incubated after (e.g., immediately after) the isolating step 76. Incubating the device can comprise incubating the device at a temperature above ambient. A person having ordinary skill in the art will recognize the optimal temperature range to facilitate spore germination and/or outgrowth of a surviving sterilant-treated test microorganism will depend upon the species of test microorganism. Thus, incubating the device can comprise incubating the device in an incubator or oven to maintain the device at a temperature that facilitates the germination and/or outgrowth of the test microorganism. In a preferred embodiment, the device is incubated in a reader that is further adapted to detect fluorescence in the at least one microchamber (e.g., a fluorescent plate reader). Incubating the device can comprise incubating the device for about 15 minutes to about 24 hours; preferably, for about 15 minutes to about 4 hours; more preferably, for about 15 minutes to about 2 hours; even more preferably, for about 15 minutes to about 1 hour.

Test microorganism viability can be determined by monitoring the metabolic activity of a germinating spore, if present, and/or the progeny of the germinating spore and/or test microorganism. The metabolic activity can be monitored conveniently and sensitively by detecting the consumption of dissolved oxygen by the respiring cells (i.e., germinating spores and progeny thereof) growing in the nutrient medium. A variety of oxygen-sensitive fluorescent compounds described herein are used in oxygen-sensing compositions to monitor the oxygen consumption by the respiring cells.

The method 600 further comprises the step 80 of detecting a presence or absence of a first fluorescent signal emitted by the oxygen sensor. As described herein, this may be done, for example, by illuminating the device with a hand-held source of electromagnetic illumination (e.g., an ultraviolet light) suitable for detecting fluorescence emitted by the fluorophore of the first fluorescent sensor. Alternatively, the device may be scanned to detect fluorescence in a microchamber using an automated plate reader. Advantageously, devices of the present disclosure can be configured to be read by an automated reader and, optionally may be used with a carrier to suitably position the device in the reader.

Detecting the presence or absence of a first fluorescent signal emitted by the first fluorescent sensor may further comprise quantifying the first fluorescent signal. The quantification of a first fluorescent signal may be performed using a variety of methods and/or instruments known in the art such as, for example, a plate reader that is configured to detect and quantify fluorescence.

The presence of oxygen in the nutrient medium can substantially quench the fluorescence of an oxygen-modulated sensor (e.g., the first fluorescent sensor of the present disclosure. Thus, if the nutrient medium isolated in the at least one microchamber is substantially saturated with ambient air, for example, the oxygen present in the nutrient medium will substantially quench the fluorescence of the first fluorescent sensor. However, if at least one of the test microorganisms survives contact with the sterilant, incubating the device can promote the growth and metabolism of the test microorganism and, thereby, reduce the dissolved oxygen in the nutrient medium to a point where the quenching is reduced and the first fluorescent sensor becomes detectably fluorescent.

In any embodiment, the method further can comprise providing a device that includes a second fluorescent sensor disposed in the at least one microchamber. The second fluorescent sensor may be a fluorescent sensor that is not modulated by oxygen. Thus, the fluorescence emitted by the second fluorescent sensor may be used as a reference signal to which the fluorescence emitted by the oxygen-modulated first fluorescent sensor can be compared. A change over time (e.g., during the incubation period) in the ratio of fluorescence emitted by the first fluorescent sensor and fluorescence emitted by the second fluorescent sensor can indicate the presence of a surviving sterilant-treated test microorganism in a microchamber and, correspondingly, a failure of the sterilization process.

In any embodiment, a method of the present disclosure further can comprise detecting a fluorescent signal from the first fluorescent sensor at a first time and at a second time after the first time. The method further can comprise comparing the fluorescent signal (e.g., the intensity of the signal) of the second fluorescent sensor measured at the first time and at the second time.

Optionally, in any embodiment, a method of the present disclosure further can comprise detecting a fluorescent signal from the second fluorescent indicator at a first time and at a second time after the first time. The method further can comprise comparing the fluorescent signal (e.g., the intensity of the signal) of the second fluorescent sensor measured at the first time and at the second time.

In some embodiments, fluorescent signals from the first and second fluorescent sensors may be detected simultaneously. In some embodiments, fluorescent signals from the first and second fluorescent sensors may be detected sequentially. Optionally, the detection can occur simultaneously while the device is incubated.

Detecting a presence of a fluorescent signal from the first fluorescent sensor may be an indicator of a failure of a sterilization process. In some embodiments, the fluorescent signal from a sterilant-treated device may be compared to a control device that is not exposed to the sterilization process. In some embodiments, the fluorescent signal from a sterilant-treated device may be quantitatively compared to a preselected threshold value to determine whether the fluorescence may be due to microbial activity.

Figure 14A:
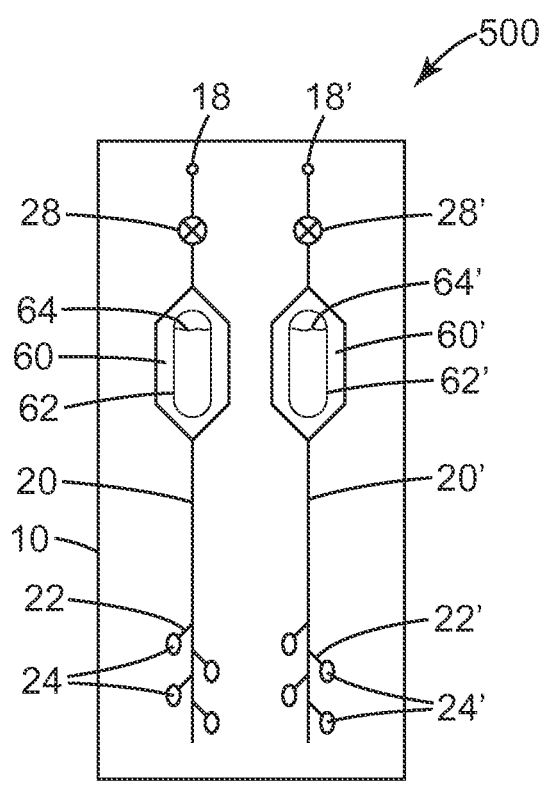
FIG. 14a is a top perspective schematic view of one embodiment of an alternative biological sterilization indicator according to the present disclosure.

In another aspect, the present disclosure provides a method for determining the effectiveness of a sterilization process. The method can comprise providing a biological sterilization indicator device comprising a plurality of microchambers distributed along two or more primary passageways, as shown in FIG. 14a. In the illustrated embodiment, the body 10 of device 500 comprises two isolated primary passageways (20 and 20', respectively), each primary passageway in fluid communication with an opening (18 and 18', respectively) and at least one microchamber (24 and 24', respectively). Each primary passageway (20 and 20', respectively) is in fluid communication with a liquid-containing reservoir (60 and 60', respectively) holding a liquid (64 and 64', respectively) such as a nutrient medium, for example. Optionally, the liquid (64 and/or 64') may be contained in a frangible container (62 and 62', respectively). Optionally, one or more microchamber 24 and/or 24' may be fluidically connected to the primary passageway 20 and/or 20' via a feeder conduit (22 and 22', respectively). In this embodiment, prior to moving a sterilant into the biological sterilization indicator device 500, one of the primary passageways (e.g., passageway 20') is closed (e.g., at valve 28') to prevent the movement of the sterilant into a microchamber 24'. Advantageously, when the valve 28' is closed and the biological sterilization indicator device 500 is exposed to a sterilization process, the test microorganisms in microchamber 24' are not exposed to the sterilant and, subsequently, can serve as a growth control (i.e., a "positive control") for the components (e.g., the test microorganisms (not shown), the nutrient medium 64, and/or the oxygen-modulated first fluorescent sensor (not shown)). After exposing the biological sterilization indicator device 500 to the sterilant, the test microorganisms in microchambers 24 and 24' each are contacted with nutrient medium 64 and isolated as described herein. The device 500 is incubated as described herein and fluorescence is detected from the first fluorescent sensor and, optionally, the second fluorescent sensor in microchambers 24 and 24', as described herein.

Figure 14B:
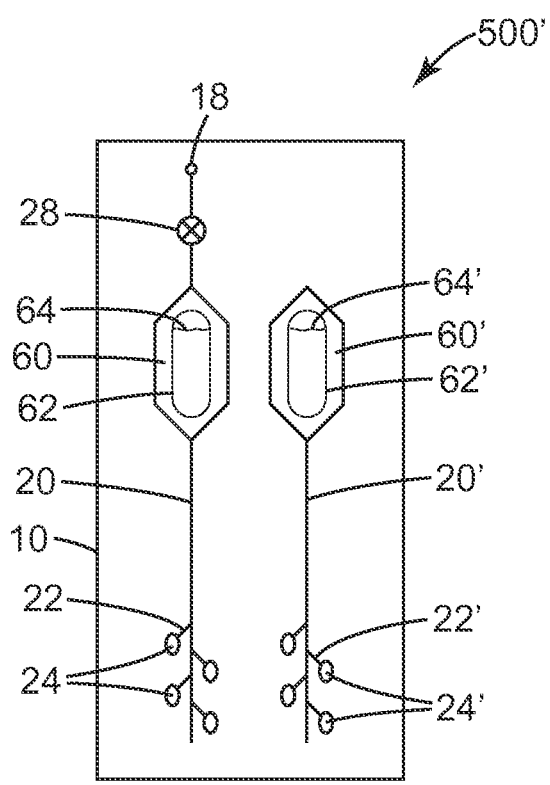
FIG. 14b is a top perspective schematic view of one embodiment of another alternative biological sterilization indicator according to the present disclosure.

It is contemplated that an alternative means to prevent the movement of the sterilant into a microchamber is to provide a biological sterilization indicator device with a configuration whereby at least one microchamber is not in fluid communication with ambience. FIG. 14b shows a device 500' having a configuration similar to the device 500 of FIG. 14a with the exception that the device 500' does not include an opening or valve (i.e., corresponding to the opening 18 and valve 28 of device 500 in FIG. 14a) in fluid communication with the primary passageway 22'. Thus, the microchambers 24' are not in fluid communication with ambience via primary passageway 20'. Accordingly, when the biological sterilization indicator device 500' is exposed to a sterilization process, the test microorganisms in microchamber 24' are not exposed to the sterilant and, subsequently, can serve as a growth control (i.e., a "positive control") for the components (e.g., the test microorganisms (not shown), the nutrient medium (64 and 64', respectively), and/or the oxygen-modulated first fluorescent sensor (not shown)). After exposing the biological sterilization indicator device 500' to the sterilant, the test microorganisms in microchambers 24 and 24' each are contacted with nutrient medium 64 and isolated as described herein. The device 500' is incubated as described herein and fluorescence is detected from the first fluorescent sensor and, optionally, the second fluorescent sensor in microchambers 24 and 24', as described herein.

In another aspect, the present disclosure provides a biological sterilization indicator system. The system can comprise any biological sterilization indicator device according to the present disclosure. The system further comprises a source of electromagnetic energy capable of stimulating the emission of a fluorescent signal by the first fluorescent sensor and a detection device (e.g., a detection device as described above) adapted to detect the fluorescent signal. In any embodiment, the detection device can be configured to be optically coupled with the biological sterilization indicator device. In any embodiment, the source and the detection device are positioned in a console (e.g., as in a plate reader, for example) that is configured to receive the device and, when the biological sterilization indicator device is received by the console, the biological sterilization indicator device is optically coupled with the detection device. In any embodiment, the system further may comprise a processor.

EMBODIMENTS

Embodiment A is a biological sterilization indicator device, comprising:
a body comprising a first layer attached to a second layer, the body forming at least one isolatable microchamber having an isolated volume of about 0.5 microliters to about 9.5 microliters and at least one primary passageway that provides fluidic communication between ambience and the at least one microchamber;
a plurality of test microorganisms disposed in the microchamber; and
an oxygen-modulated first fluorescent sensor disposed in the microchamber.

Embodiment B is the device of Embodiment A, wherein the plurality of test microorganisms comprises a first plurality of first test microorganisms disposed in a first isolatable microchamber, the device further comprising a second plurality of second test microorganisms disposed in a second isolatable microchamber, and wherein the oxygen-modulated first fluorescent sensor is disposed in each of the first and second microchambers.

Embodiment C is the device of Embodiment B, wherein the first test microorganisms and the second test microorganisms comprise test microorganisms of the same species.

Embodiment D is the device of Embodiment B, wherein the first test microorganisms comprise test microorganisms of a different species than the second test microorganisms.

Embodiment E is the device of any one of the preceding Embodiments, wherein at least one of the pluralities of test microorganisms comprises a plurality of spores.

Embodiment F is the device of any one of the preceding Embodiments, further comprising at least one liquid-containing reservoir, the reservoir having a closed state in which the liquid is not in fluid communication with one or more of the microchambers and an open state in which the liquid is in fluid communication with at least one of the one or more of the microchambers.

Embodiment G is the device of Embodiment F, wherein the volume of liquid in the reservoir is equal to or greater than the isolated volume of the one or more microchambers with which it is in fluid communication.

Embodiment H is the device of any one of the preceding Embodiments, wherein the at least one primary passageway is adapted to provide selective fluidic communication between ambience and the at least one microchamber.

Embodiment I is device of Embodiment H, wherein the primary passageway comprises a valve.

Embodiment J is the device of any one of Embodiment H or Embodiment I, wherein the at least one primary passageway is further configured to provide fluidic communication between the at least one reservoir and the at least one chamber.

Embodiment K is the device of any one of Embodiments F through I, further comprising at least one branch conduit, wherein the at least one branch conduit provides fluid communication between the at least one reservoir and at least one microchamber.

Embodiment L is device of any one of the preceding Embodiments, further comprising a second fluorescent sensor that is not substantially modulated by oxygen, wherein the second fluorescent sensor is disposed in at least one microchamber.

Embodiment M is the device of any one of the preceding Embodiments, wherein the first and/or second fluorescent sensor comprises a bead, a film, or a coating.

Embodiment N is the device of Embodiment M, wherein the coating comprises a water-insoluble coating.

Embodiment O is the device of Embodiment M, wherein the coating comprises a water-soluble coating.

Embodiment P is the device of Embodiment O, wherein the coating further comprises the plurality of test microorganisms.

Embodiment Q is the device of any one of Embodiments H through P, wherein the at least one primary passageway is sealable.

Embodiment R is the device of any one of Embodiments H through Q, wherein the at least one first and/or second passageways further comprises at least two feeder conduits, wherein each feeder conduit of the at least two feeder conduits is in fluid communication with one of two separate microchambers of the plurality of microchambers.

Embodiment S is the device of any one of the preceding Embodiments, wherein at least one of the plurality of test microorganisms in at least one microchamber consists of spores of the species *Geobacillus stearothermophilus* or spores from the species *Bacillus atrophaeus*.

Embodiment T is the device of any one of Embodiments B through S, wherein the device comprises a first microchamber and a second microchamber, wherein the first plurality of test microorganisms in the first microchamber consists of spores of the species *Geobacillus stearothermophilus* and spores from the species *Bacillus atrophaeus*.

Embodiment U is the device of any one of Embodiments B through S, wherein the device comprises a first microchamber and a second microchamber, wherein the first plurality of test microorganisms disposed in the first microchamber consists of spores of the genus *Geobacillus stearothermophilus*, wherein the second plurality of test microorganisms disposed in the second microchamber consists of spores of the genus *Bacillus atrophaeus*.

Embodiment V is the device of any one of the preceding Embodiments, wherein the liquid in the reservoir is contained in a frangible container.

Embodiment W is the device of any one of the preceding Embodiments, wherein the liquid comprises a nutrient.

Embodiment X is the device of any one of the preceding Embodiments, wherein the at least one microchamber comprises a first wall and a second wall, wherein the first wall or second wall is substantially non-transmissive to wavelengths of light in the u.v.-visible electromagnetic spectrum.

Embodiment Y is the device of Embodiment X, wherein the second wall comprises a white-colored portion.

Embodiment Z is the device of Embodiment X or Embodiment Y, wherein the second wall comprises a reflective portion.

Embodiment AA is the device of Embodiment Z, wherein the second wall comprises metal, a metal foil, or a metal-coated substrate.

Embodiment BB is the device of any one of Embodiments X through AA, wherein the second wall comprises a black-colored portion.

Embodiment CC is the device of any one of Embodiments X through BB, wherein the first wall is more transmissive to wavelengths of light in the u.v.-visible electromagnetic spectrum than the second wall.

Embodiment DD is the device of any one of the preceding Embodiments, further comprising a secondary growth indicator system comprising a pH indicator.

Embodiment EE is the device of any one of Embodiments B through DD, wherein the device comprises a first microchamber and a second microchamber, wherein the first microchamber has disposed therein a first plurality of test microorganisms consisting of at least about 10 times as many spores as a number of test microorganisms disposed in the second microchamber.

Embodiment FF is the device of any one of the preceding embodiments, wherein wherein the first layer is substantially impermeable to oxygen.

Embodiment GG is the device of any one of the preceding Embodiments, wherein the second layer is substantially impermeable to oxygen.

Embodiment HH is a biological sterilization indicator system comprising:

a biological sterilization indicator device according to any one of the preceding Embodiments;

a source of electromagnetic energy capable of stimulating the emission of a fluorescent signal by the first fluorescent sensor; and a detection device adapted to detect the fluorescent signal.

Embodiment II is the biological sterilization indicator system of Embodiment HH, wherein the detection device is configured to be optically coupled with the biological sterilization indicator device.

Embodiment JJ is the biological sterilization indicator system of Embodiment HH or Embodiment II, wherein the source and the detection device are positioned in a console that is configured to receive the biological sterilization indicator device and wherein, when the biological sterilization indicator device is received by the console, the biological sterilization indicator device is optically coupled with the detection device.

Embodiment KK is a method for determining the effectiveness of a sterilization process, the method comprising:

providing a biological sterilization indicator device according to any one of Embodiments A-GG;

moving a sterilant into fluidic communication with the at least one microchamber to form sterilant-treated test microorganisms;

contacting the sterilant-treated test microorganisms with a nutrient medium in at least one microchamber;

isolating the at least one microchamber such that a total volume of the nutrient medium and sterilant-treated test microorganisms isolated in the at least one microchamber is about 9.5 microliters or less;

after isolating the microchamber, incubating the device for a period of time; and detecting a presence or absence of a first fluorescent signal emitted by the first fluorescent sensor.

Embodiment LL is the method of Embodiment KK, wherein the device comprises a first microchamber and a second microchamber, wherein moving a sterilant into fluid communication comprises moving the sterilant into fluid communication with the first and second microchambers.

Embodiment MM is the method of Embodiment KK, wherein the device comprises a first microchamber and a second microchamber, wherein moving a sterilant into fluidic communication with the first microchamber to form sterilant-treated test microorganisms further comprises preventing movement of the sterilant into fluidic communication with the second microchamber; wherein detecting a presence or absence of a first fluorescent signal emitted by the first fluorescent sensor further comprises detecting a presence or absence of a first fluorescent signal emitted by the first fluorescent sensor in both the first microchamber and the second microchamber.

Embodiment NN is the method of any one of Embodiments KK through MM, wherein moving a sterilant into fluidic communication comprises opening at least one valve to provide fluidic communication between ambience and the at least one microchamber.

Embodiment OO is the method of any one of Embodiments KK through NN, wherein contacting the sterilant-treated test microorganisms with the nutrient liquid further comprises providing an external force to move the liquid into at least one microchamber.

Embodiment PP is the method of Embodiment OO, wherein providing the external force comprises providing a centripetal force.

Embodiment QQ is the method of any one of Embodiments KK through PP, wherein incubating the device comprises incubating the device about 15 minutes to about 24 hours.

Embodiment RR is method of any one of Embodiments KK through QQ, wherein detecting a presence or absence of a first fluorescent signal comprises detecting the first fluorescent signal at a first time and detecting the first fluorescent signal at a second time after the first time.

Embodiment SS is the method of Embodiment RR, further comprising comparing the first fluorescent signal detected at the first time with the first fluorescent signal detected at the second time.

Embodiment TT is the method of any one of Embodiments KK through SS, wherein the device comprises the second fluorescent sensor, wherein the second fluorescent sensor is disposed in at least one microchamber, wherein the method further comprises detecting a second fluorescent signal from the second fluorescent sensor.

Embodiment UU is the method of Embodiment TT, wherein detecting the second fluorescent signal comprises detecting the second fluorescent signal at a first time and detecting the second fluorescent signal at a second time after the first time.

Embodiment VV is the method of Embodiment UU, further comprising comparing the second fluorescent signal detected at the first time with the second fluorescent signal detected at the second time.

Embodiment WW is the method of any one of Embodiments KK through VV, wherein detecting the first or second fluorescent signal further comprises measuring the intensity of the first or second fluorescent signal.

Embodiment XX is the method of Embodiment WW, further comprising comparing the intensity of the first fluorescent signal to the intensity of the second fluorescent signal.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials.

Materials utilized in the preparation of the examples are shown in Table 1

TABLE 1

List of Materials

| Material | Source |
|---|---|
| Assay device | As disclosed in U.S. Pat. No. 6,627,159 |
| Sensor beads | From OxoPlate Part Number OP96C; PreSens - Precision Sensing GmbH; Regensberg, DE |
| Silicone polyurea adhesive | Disclosed in WO 2003/052019 |
| Cover tape | Applied Biosystems MicroAmp Part No. 4311971; Life Technologies Corporation; Carlsbad, CA |

Example 1

Assembly of a Biological Sterilization Indicator

Devices having a liquid loading reservoir connected to an array of reagent reservoirs via a channel were fabricated as described in U.S. Pat. No. 6,627,159. A first layer comprising a polypropylene film (approximately 0.57 mm thick) was subjected to a thermoform process to produce topological features.

Oxygen sensor beads were removed from a commercially available 96 well plate (OxoPlate Part Number OP96C, PreSens GmbH, Germany) by washing the wells of the plate with methanol. The beads were extracted from 8 wells, transferred to an Eppendorf tube, pelleted via centrifugation, and washed 3X with methanol. The bead pellet was resuspended in 15 microliters of water. One microliter of the bead suspension was pipetted into each well containing the dried spore suspension and the first layer was dried by placing it in an incubator at 37° C. for 10 minutes.

One microliter aliquots of two aqueous suspensions of $B.$ $subtilis$ spores (either $5\times10^8$ or $5\times10^9$ spores/mL) were pipetted into separate wells (each well containing the dried-down bead suspension) of the thermoformed first layer. The water from the suspensions was allowed to evaporate from the spore-inoculated wells by incubating the first layer at 37° C. for 10 minutes.

After the wells were dry, a second layer comprising adhesive-coated (a steam-compatible silicone polyurea adhesive of the type disclosed in International Patent Publication No. WO 2003/052019) aluminum foil film was placed onto the first layer and pressure was applied against the second layer to bond the adhesive to the first layer. In addition, a small blunt stylus (the tip of a forceps having a width of approximately 750 microns) was used to apply pressure around the perimeter of the first layer to ensure complete bonding. The finished device had a configuration similar to the device shown in FIG. 1 of International Patent Publication No. WO 02/01180 except that each device had one process array that comprised 48 microwells (chambers). Each microchamber had a volume of approximately 1.5 microliters.

Example 2

Detection of Viable Spores in a Biological Sterilization Indicator Device

Figure 13A:
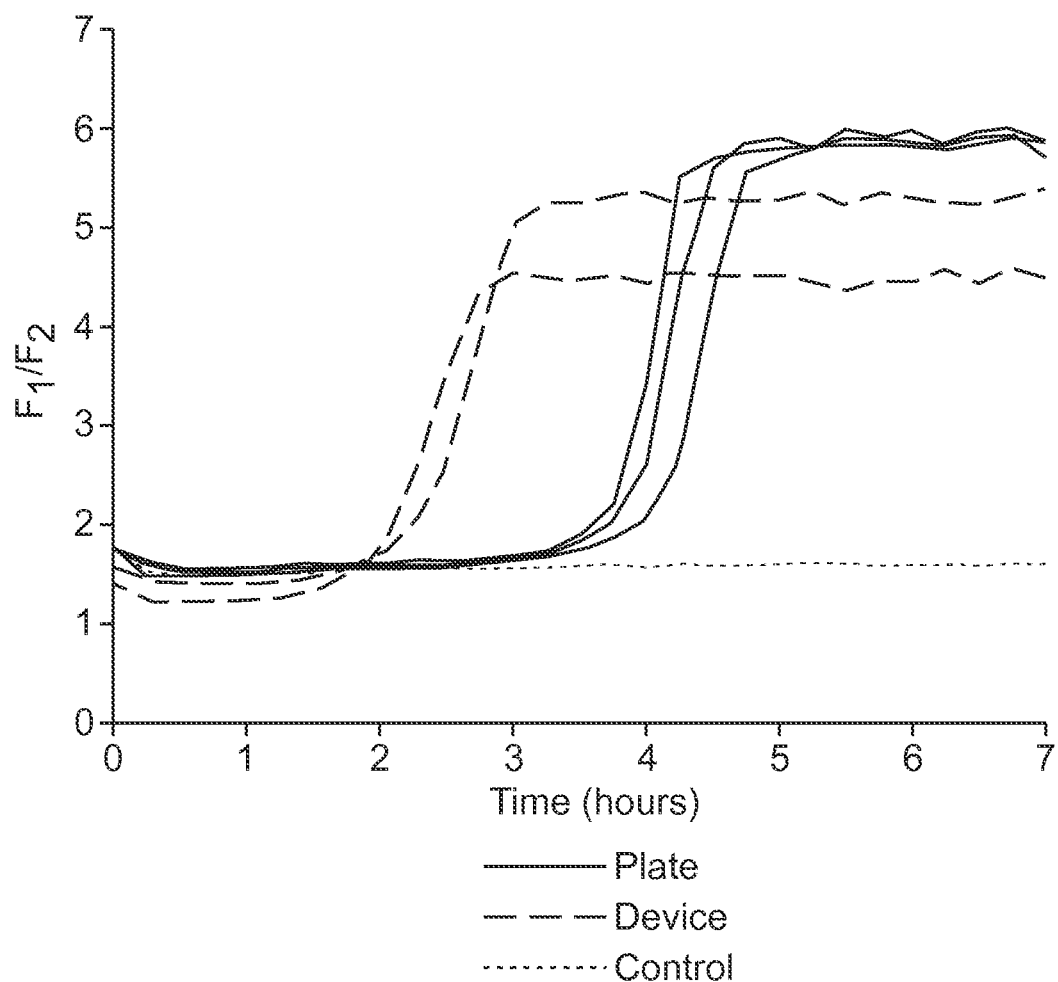
FIG. 13a is a graph of relative fluorescence detected after various lengths of incubation of a device of the present disclosure containing about $5 \times 10^5$ spores.
Figure 13B:
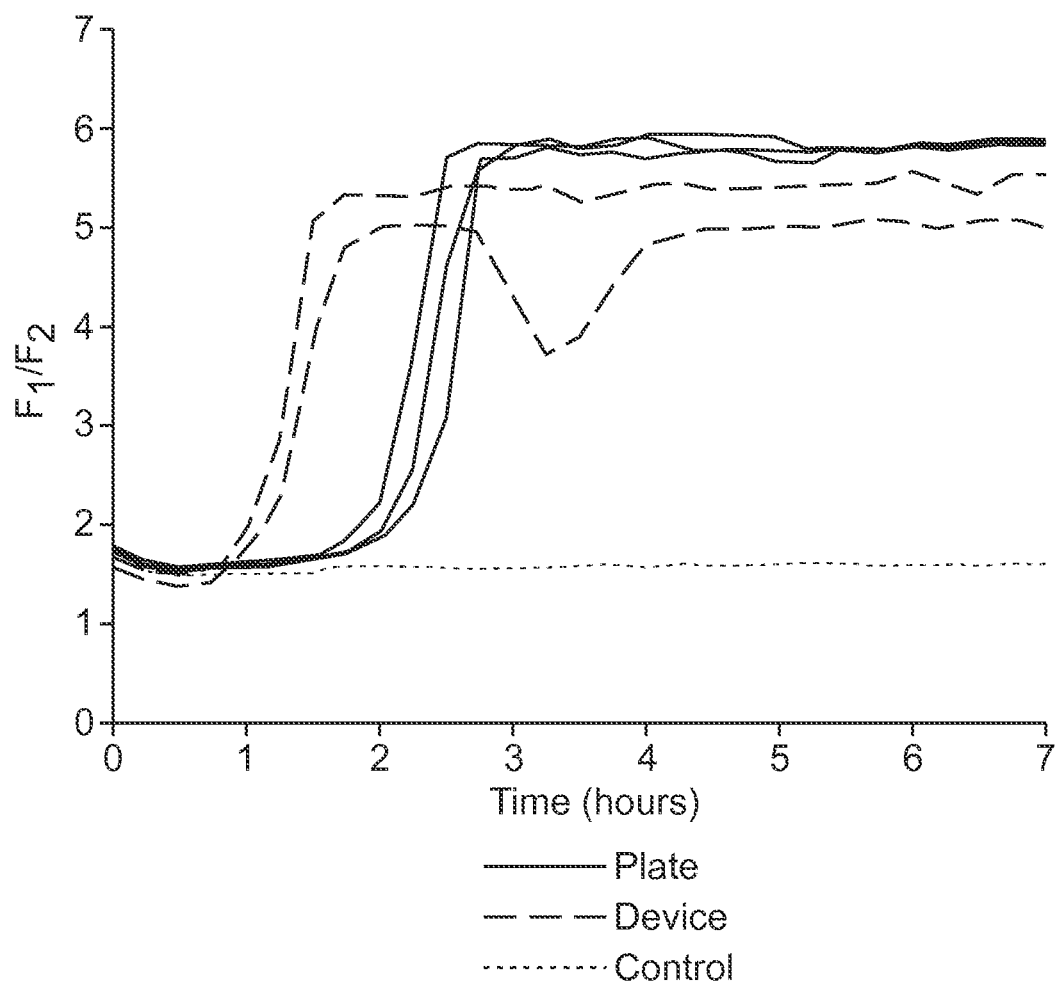
FIG. 13b is a graph of relative fluorescence detected after various lengths of incubation of a device of the present disclosure containing about $5 \times 10^6$ spores.

Biological Sterilization Indicator devices were prepared as described in Example 1. Thirty microliters of nutrient media (17 g/L bacteriological peptone and 0.17 g/L L-alanine dissolved in deionized water with the pH adjusted to 7.6) was added to each loading structure of the process arrays and the nutrient media was distributed into each well by centrifugation (the device was placed into a 15 mL centrifuge tube, which was placed into a swinging bucket rotor and centrifuged at 2,000 rpm for 2 minutes). The indicator device was placed in a fluorescence plate reader (TECAN Infinite Plate Reader Model No. M200, Tecan Group Ltd., Männedorf, C H) heated to 37° C. The devices were scanned for fluorescence every 15 minutes and the rate of oxygen consumption was monitored as a function of time according to the manufacturer instructions accompanying the OxoPlate 96-well plates. An increase in the oxygen bead to control bead fluorescence ratio indicated a decrease in oxygen concentration in the media resulting from spore germination and growth. The results are shown in FIGS. 13*a* and 13*b*.

Comparative Example 1

Detection of Viable Spores in a Biological Sterilization Indicator Device

One microliter aliquots of the same spore dilutions used in Example 1 were pipetted into the wells of an OxoPlate 96-well plate. Two hundred microliters of nutrient media (same as the media used in Example 2) was added to the wells of the OxoPlate 96-well plate. The plate was covered with PCR cover tape (Applied Biosystems MicroAmp Part No. 4311971, Life Technologies Corporation; Carlsbad, Calif.). The covered plates were placed in a heated (37° C.) fluorescence plate reader and the plates were scanned and analyzed as described in Example 2. The results are shown in FIGS. 13*a* and 13*b*. The results show fluorescence due to the metabolism of oxygen by the spores was detected at least one hour earlier (i.e., about 50% faster) in the microwell device, compared to the 96-well plates, when each well contained $5 \times 10^5$ spores. In addition, the results show fluorescence due to the metabolism of oxygen by the spores was detected about 2 hours earlier (i.e., about 50% faster) in the microwell device, compared to the 96-well plates, when each well contained $5 \times 10^6$ spores.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A biological sterilization indicator device, comprising:
a body comprising a first layer, a second layer, and an adhesive layer between the first layer and the second layer; wherein the adhesive layer covers an entire surface of the second layer facing the first layer and wherein the adhesive layer attaches the first layer to the second layer, the body forming between the first layer and the adhesive layer:
at least one isolatable microchamber having an isolated volume of about 0.5 microliters to about 9.5 microliters,
at least one primary passageway that provides fluidic communication between ambience and the at least one microchamber, and
a feeder conduit;
a deformable seal located in the primary passageway or within the feeder conduit to provide selective fluidic communication between ambience and the at least one microchamber, wherein the deformable seal comprises a plastically deformed portion of at least one of the first layer and the second layer, wherein in the plastically deformed portion the adhesive layer adheres the first layer to the second layer to occlude at least one of the primary passageway or the feeder conduit;
a plurality of aerobic test microorganisms disposed in the microchamber; and
an oxygen-modulated first fluorescent sensor disposed in the microchamber, wherein the isolatable microchamber comprises a first wall and a second wall, wherein the first wall of the isolatable microchamber comprises a portion of the first layer and the second wall comprises a portion of the second layer,
wherein the biological sterilization indicator device is suitable to be exposed to steam.

2. The device of claim 1, wherein the plurality of test microorganisms comprises a first plurality of first test microorganisms disposed in a first isolatable microchamber, the device further comprising a second plurality of second test microorganisms disposed in a second isolatable microchamber, and wherein the oxygen-modulated first fluorescent sensor is disposed in each of the first and second microchambers.

3. The device of claim 1, further comprising at least one liquid-containing reservoir, the reservoir having a closed state in which the liquid is not in fluid communication with one or more of the microchambers and an open state in which the liquid is in fluid communication with at least one of the one or more of the microchambers.

4. The device of claim 3, further comprising at least one branch conduit, wherein the at least one branch conduit provides fluid communication between the at least one reservoir and at least one microchamber.

5. The device of claim 1, further comprising a second fluorescent sensor that is not substantially modulated by oxygen, wherein the second fluorescent sensor is disposed in at least one microchamber.

6. The device of claim 1, wherein the at least one primary passageway further comprises at least two feeder conduits, wherein each feeder conduit of the at least two feeder conduits is in fluid communication with one of two separate microchambers of the plurality of microchambers.

7. The device of claim 2, wherein the device comprises a first microchamber and a second microchamber, wherein the first plurality of test microorganisms in the first microchamber consists of spores of the species *Geobacillus stearothermophilus* and spores from the species *Bacillus atrophaeus*.

8. The device of claim 2, wherein the device comprises a first microchamber and a second microchamber, wherein the first plurality of test microorganisms disposed in the first microchamber consists of spores of the genus *Geobacillus stearothermophilus*, wherein the second plurality of test microorganisms disposed in the second microchamber consists of spores of the genus *Bacillus atrophaeus*.

9. The device of claim 1, wherein the at least one isolatable microchamber comprises a first wall and a second wall, wherein the first wall or second wall is substantially non-transmissive to wavelengths of light in the u.v.-visible electromagnetic spectrum.

10. The device of claim 9, wherein the second wall comprises a black-colored portion.

11. The device of claim 9, wherein the first wall is more transmissive to wavelengths of light in the u.v.-visible electromagnetic spectrum than the second wall.

12. The device of claim 2, wherein the device comprises a first microchamber and a second microchamber, wherein the first microchamber has disposed therein a first plurality of test microorganisms consisting of at least about 10 times as many spores as a number of test microorganisms disposed in the second microchamber.

13. A biological sterilization indicator system comprising:
a biological sterilization indicator device according to claim 1;
a source of electromagnetic energy capable of stimulating the emission of a fluorescent signal by the first fluorescent sensor; and
a detection device adapted to detect the fluorescent signal.

14. The biological sterilization indicator system of claim 13, wherein the source and the detection device are positioned in a console that is configured to receive the biological sterilization indicator device and wherein, when the biological sterilization indicator device is received by the console, the biological sterilization indicator device is optically coupled with the detection device.

15. A method for determining the effectiveness of a sterilization process, the method comprising:
providing a biological sterilization indicator device according to claim 1;
moving a sterilant into fluidic communication with the at least one microchamber to form sterilant-treated test microorganisms;
contacting the sterilant-treated test microorganisms with a nutrient medium in at least one microchamber;
isolating the at least one microchamber such that a total volume of the nutrient medium and sterilant-treated test microorganisms isolated in the at least one microchamber is about 9.5 microliters or less;
after isolating the microchamber, incubating the device for a period of time; and
detecting a presence or absence of a first fluorescent signal emitted by the first fluorescent sensor.

16. The method of claim 15, wherein the device comprises a first microchamber and a second microchamber, wherein moving a sterilant into fluid communication comprises moving the sterilant into fluid communication with the first and second microchambers.

17. The method of claim 15, wherein the device comprises a first microchamber and a second microchamber, wherein moving a sterilant into fluidic communication with the first microchamber to form sterilant-treated test microorganisms further comprises preventing movement of the sterilant into fluidic communication with the second microchamber; wherein detecting a presence or absence of a first fluorescent signal emitted by the first fluorescent sensor further comprises detecting a presence or absence of a first fluorescent signal emitted by the first fluorescent sensor in both the first microchamber and the second microchamber.

18. The method of claim 15, wherein the device comprises a second fluorescent sensor, wherein the second fluorescent sensor is disposed in at least one microchamber, wherein the method further comprises detecting a second fluorescent signal from the second fluorescent sensor.

\* \* \* \* \*

UNITED STATES PATENT AND TRADEMARK OFFICE
CERTIFICATE OF CORRECTION

PATENT NO. : 10,947,577 B2  
APPLICATION NO. : 14/377203  
DATED : March 16, 2021  
INVENTOR(S) : Francois Ahimou et al.

Page 1 of 1

It is certified that error appears in the above-identified patent and that said Letters Patent is hereby corrected as shown below:

In the Specification

Column 1  
Line 7        After "application" insert -- is a national stage filing under 35 U.S.C. 371 of PCT/US2013/025500, filed Feb. 11, 2013, which --.  
Line 7        Delete "the benefit of" and insert -- priority to --, therefor.  
Line 8        After "2012," insert -- the disclosure of --.  
Line 9        After "incorporated" delete "herein".  
Line 9        Delete "entirety." and insert -- entirety herein. --, therefor.

Column 16  
Lines 4-5    Delete "polyvinylpyrollidone," and insert -- polyvinylpyrrolidone, --, therefor.

Column 24  
Line 14       Delete "wherein wherein" and insert -- wherein --, therefor.

Column 27  
Line 10       Delete "C H)" and insert -- CH) --, therefor.

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*